United States Patent
Bühlmayer et al.

Patent Number: 5,610,153
Date of Patent: Mar. 11, 1997

[54] BENZAZEPINONE DERIVATIVES

[75] Inventors: Peter Bühlmayer, Arlesheim, Switzerland; Pascal Furet, Thann, France

[73] Assignee: Ciba-Geigy Corporation, Tarrytown, N.Y.

[21] Appl. No.: 454,106

[22] PCT Filed: Dec. 6, 1993

[86] PCT No.: PCT/EP93/03426

§ 371 Date: Jul. 12, 1995

§ 102(e) Date: Jul. 12, 1995

[87] PCT Pub. No.: WO94/13651

PCT Pub. Date: Jun. 23, 1994

[30] Foreign Application Priority Data

Dec. 11, 1992 [CH] Switzerland .............................. 3801/92

[51] Int. Cl.⁶ .......................... A61K 31/55; C07D 513/04
[52] U.S. Cl. .............................................. 514/211; 540/491
[58] Field of Search .............................. 540/491; 514/211

[56] References Cited

U.S. PATENT DOCUMENTS 4,477,464  10/1984  Slade et al. .............................. 540/491

FOREIGN PATENT DOCUMENTS 0135349  3/1985  European Pat. Off. ................ 540/491

*Primary Examiner*—Robert T. Bond
*Attorney, Agent, or Firm*—Marla J. Mathias; Henry P. Nowak; Gregory D. Ferraro

[57] ABSTRACT

The invention relates to substituted 3-amino-1-arylalkyl-benzazepin-2-ones of the general formula

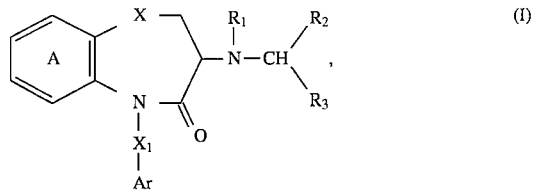

wherein Ar is aryl;

X is —O— or —S(O)$_n$— and n is 0, 1 or 2;

X$_1$ is C$_1$-C$_2$alkylene or a direct bond;

R$_1$ is hydrogen, lower alkyl, aryl-lower alkyl or acyl;

R$_2$ is lower alkyl, hydroxy-lower alkyl, lower alkoxy-lower alkyl, aryl-lower alkoxy-lower alkyl, aryl-lower alkyl or C$_3$-C$_7$cycloalkyl-lower alkyl;

R$_3$ is carboxy; lower alkoxycarbonyl; lower alkoxy-lower alkoxycarbonyl; aryl-lower alkoxycarbonyl; aryloxycarbonyl; carbamoyl; carbamoyl that (i) is monosubstituted by hydroxy, lower alkanesulfonyl, halo-lower alkanesulfonyl or by arylsulfonyl, (ii) is monosubstituted or disubstituted, the substituents being independent of one another, by lower alkyl, lower alkenyl, lower alkynyl or by phenyl-lower alkyl or (iii) is disubstituted by lower alkylene or by lower alkylene-Z$_1$-lower alkylene, Z$_1$ being O, S or NH; 5-tetrazolyl; PO$_2$H$_2$; PO$_3$H$_2$ or SO$_3$H$_2$; the ring A and aromatic radicals are, independently of one another, unsubstituted or mono- or poly-substituted by substituents selected from the group consisting of: lower alkyl, aryl-lower alkyl, lower alkoxy-lower alkyl, lower alkoxy, lower alkoxy-lower alkoxy, aryl-lower alkoxy, C$_3$-C$_7$cycloalkyl, C$_3$-C$_7$cycloalkyl-lower alkyl, nitro, halogen, trifluoromethyl, amino and amino that is monosubstituted or disubstituted, the substituents being independent of one another, by lower alkyl, aryl-lower alkyl or by aryl, or disubstituted by lower alkylene or by lower alkyleneoxy-lower alkylene;

or a salt thereof; to processes for the preparation thereof; and to the use thereof as well as to pharmaceutical compositions that comprise compounds of formula (I) or pharmaceutically acceptable salts thereof.

18 Claims, No Drawings

BENZAZEPINONE DERIVATIVES

The invention relates to substituted 3-amino-1-arylalkyl-benzazepin-2-ones of the general formula

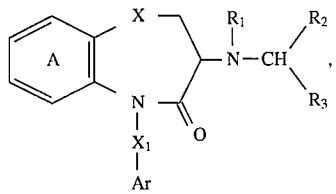

wherein

Ar is aryl;

X is —O— or —S(O)$_n$— and n is 0, 1 or 2;

X$_1$ is C$_1$-C$_2$alkylene or a direct bond;

R$_1$ is hydrogen, lower alkyl, aryl-lower alkyl or acyl;

R$_2$ is lower alkyl, hydroxy-lower alkyl, lower alkoxy-lower alkyl, aryl-lower alkoxy-lower alkyl, aryl-lower alkyl or C$_3$-C$_7$cycloalkyl-lower alkyl;

R$_3$ is carboxy; lower alkoxycarbonyl; lower alkoxy-lower alkoxycarbonyl; aryl-lower alkoxycarbonyl; aryloxycarbonyl; carbamoyl; carbamoyl that (i) is monosubstituted by hydroxy, lower alkanesulfonyl, halo-lower alkanesulfonyl or by arylsulfonyl, (ii) is monosubstituted or disubstituted, the substituents being independent of one another, by lower alkyl, lower alkenyl, lower alkynyl or by phenyl-lower alkyl or (iii) is disubstituted by lower alkylene or by lower alkylene-Z$_1$-lower alkylene, Z$_1$ being O, S or NH; 5-tetrazolyl; PO$_2$H$_2$; PO$_3$H$_2$ or SO$_3$H$_2$;

the ring A and aromatic radicals are, independently of one another, unsubstituted or mono- or poly-substituted by substituents selected from the group consisting of: lower alkyl, aryl-lower alkyl, lower alkoxy-lower alkyl, lower alkoxy, lower alkoxy-lower alkoxy, aryl-lower alkoxy, C$_3$-C$_7$cycloalkyl, C$_3$-C$_7$cycloalkyl-lower alkyl, nitro, halogen, trifluoromethyl, amino and amino that is monosubstituted or disubstituted, the substituents being independent of one another, by lower alkyl, aryl-lower alkyl or by aryl, or disubstituted by lower alkylene or by lower alkyleneoxy-lower alkylene;

or salts thereof; to processes for the preparation thereof; and to the use thereof as well as to pharmaceutical compositions that comprise compounds of formula (I) or pharmaceutically acceptable salts thereof.

There are described in the literature two receptor subtypes [AT$_1$ and AT$_2$] of angiotensin(II) which differ in respect of their different affinities for synthetic angiotensin-II analogues.

AT$_2$-receptors can be identified in various body tissues. Such receptors are described in the relevant literature as being expressed, for example, in neuron tumour cells, in transformed neural cells, in various regions of the central nervous system, in the heart and the arteries, in female reproductive organs, such as the uterus and the ovaries, in the adrenal glands and the pancreas and also in healing skin.

Surprisingly, the compounds of the present invention exhibit selective binding to the angiotensin-II-AT$_2$-receptor in the model described by Whitebread et al., *Biochem. Biophys. Res. Comm.* 1989, 163, 184–191. Those binding properties of the compounds according to the invention were detected below a concentration of 50 μmol/l. Accordingly, the compounds according to the invention may be used especially in the prophylactic or therapeutic treatment of symptoms that are caused by AT$_2$-receptors.

It has been demonstrated that an AT$_2$-receptor stimulation modulates the protein tyrosine phosphatase in the rat phaeochromocytoma cell line PC12W and in AT$_2$-receptor transfected COS cells [Botari et al. *Biochem. Biophys. Res. Commun.* 1992, 183, 206–211; Botari et al., *Front. Neuroendocrinol.* 1993, 44, 207–213; Brechler et al., *Regul. Peptide* 1993, 44, 207–213; Kambayashi et al., *J. Biol. Chem.* 1993, 268, 24543–24546]

inhibits the guanylate cyclase in PC12W and neuron cultures [Botari et al., *Biochem. Biophys. Res. Commun.* 1992, 183, 206–211; Botari et al., Front, *Neuroendocrinol*, 1993, 44, 207–213; Brechler et al., *Regul. Peptide* 1993, 44, 207–213: Summers et al., *Am. J. Physiol.* 1991, 260, 679–687; Summers et al., *Proc. Natl. Acad. Sci.* USA 1991, 88, 7567–7571] and modulates T-type Ca$^{++}$ flows in neuroblastoma NG108-15 cells [Buisson et al., *FEBS* 1992, 309, 161–164].

In addition, the AT$_2$-receptor is involved in cell growth and cell proliferation, since it is especially expressed in high density during foetal development [Grady et al., *J. Clin. Invest.* 1991, 88 921–933].

As a result of the ability of AT$_2$-ligands to inhibit the proliferation of vascular endothelial cells, and since endothelial cell proliferation is the cause of angiogenesis, which is in turn a prerequisite for tumour growth and the development of metastases, the compounds according to the invention may be used in the treatment of cancer and those disorders generally associated with benign and malignant proliferation.

AT$_2$-receptors also bring about the modulation of phosphotyrosine phosphatase activity (PTPase activity), which is associated with growth-inhibiting and antiproliferative effects. AT$_2$-receptors are expressed in vascular smooth muscle cells during neointimal development. The compounds according to the invention may therefore be used in the treatment of vascular proliferation disorders, including vascular cell wall hypertrophy, which follows a thrombosis, angioplasty, Buerger's disease, atherosclerosis and arteriosclerosis.

The modulation of PTPase activity also plays a part in connection with the action of insulin, which is mediated by a tyrosine kinase receptor and a signal pathway for the tyrosine-phosphorylation/dephosphorylation enzyme system. Accordingly, the compounds according to the invention may also be used in the treatment of diabetic disorders and complications, including diabetic neuropathy, nephropathy and vasculopathy.

AT$_2$-receptors also regulate the diameter of cerebral arteries and thus cerebral blood flow, and are thus suitable for the treatment of cerebral ischaemia and strokes and associated symptoms.

A further important field of treatment arises from the fact that AT$_2$-receptors are localised in selective areas of the brain that are associated with the control of motor activity, of sensory and visual phenomena and of the limbic system, and with the regulation of appetite. Similarly, calcium flows, which are associated with the control of neurosecretion and electrical activity, are modulated by AT$_2$-receptors. Accordingly, the compounds according to the invention may be used in the treatment and diagnosis of numerous neurological, psychiatric, neuroendocrinal, neurodegenerative and neuroimmunological disorders, including disorders associated with dependency, anxiety states, depression, epilepsy, memory, psychoses, pain, sleep, tardive dyskinesia, hyperactivity and Petit Mal, and disorders associated with the regulation of autonomous functions, and also in the treatment of Parkinson's disease, Alzheimer's disease and appetite disorders and associated phenomena, such as obesity and anorexia.

Since, as mentioned, $AT_2$-receptors influence PTPase activity, and such receptors have also been identified in healing skin, the compounds according to the invention can also modulate cell growth and the differentiation of the skin and play a part in the reorganisation of skin tissue, thereby promoting the healing of wounds and preventing keloid formation. $AT_2$-receptors that exert a regulatory effect on ovulation have also been found in ovarian follicle cells. To that extent the compounds according to the invention may be used to treat sterility that has been caused by anovulation, ovulation disorders, dysfunction of the corpus luteum, missed abortion and also other such disorders that are associated with ovary dysfunction, including premenstrual syndrome and dysmenorrhoea.

There is a high density of $AT_2$-receptors in the human myometrium. As a result of the stimulation of PTPase activity, contraction of the uterus can be inhibited, and the compounds according to the invention may be used in the treatment of disorders caused by abnormal uterus contraction, including dysmenorrhoea, missed abortion, hypertrophy and hyperkinesia.

Similarly, PTPase activity can also modulate the activity of tyrosine kinase and other enzymes associated with cell proliferation and cell differentiation, as a result of which the compounds according to the invention may also be used in the treatment and prophylaxis of fibromas of the uterus.

$AT_2$-receptors play a part in the regulation of cardiac function. The demonstrated effect of $AT_2$-receptors on T-type calcium flow may play an important part in the heart in arrhythmogenesis and in the modulation of pace-maker function in the sinoauricular node. Accordingly, the compounds of the present invention may be used in the treatment of cardiac insufficiency and arrhythmia. They are furthermore useful in the treatment of cardiac hypertrophy, since $AT_2$-receptors cause an increase in PTPase activity, which is generally to be regarded as growth-inhibiting.

$AT_2$-receptors are furthermore found in the zona glomerulosa, zona fasciculata and medulla of the adrenal glands. Since T-type calcium flows are modulated and, furthermore, anti-proliferative properties are imparted by those receptors, the compounds according to the invention may be used in the treatment of hypertrophy and hypersecretion of the adrenal cortex, such as Cushing's syndrome, adrogenital syndrome and primary hyperaldosteronism.

The modulation of T-type calcium flows enables the compounds according to the invention to be used in the treatment of disorders involved with the deregulation of the pancreas and exocrinal secretion, such as pancreatitis, hyperinsulinism and Zollinger-Ellison syndrome.

There is a special need for medicaments to be available for the treatment of post myocardial infarction in order effectively to treat cardiac failure following a cardiac infarction. An appropriate therapy should advantageously be undertaken after the repairing and healing phase of the heart. An acute myocardial infarction is known to cause both a change in haemodynamic effects and an alteration in structure in the damaged and healthy zones of the heart. Thus, a myocardial infarction reduces, for example, the maximum cardiac output and the stroke volume. Those haemodynamic effects can be ascertained in a manner known per se, for example in the rat model [Schoemaker et al. *J.Mol.CellCardiol.* 23, 187–197 (1991)]. Also associated with myocardial infarction is a stimulation of the DNA synthesis occurring in the interstice as well as an increase in the formation of collagen in the areas of the heart not affected [van Krimpen et al. *J. Mol. CellCardiol.* 23, 1245–1253 (1991)].

Surprisingly, the compounds according to the invention and the salts thereof reduce the DNA synthesis. Also, the post-myocardial treatment causes an improvement in the negative haemodynamic effects. Those regulatory effects are attributable to the binding of the compounds to the $AT_2$-receptor. These findings are obtained using the methodology, known per se, according to Schoemaker et al., *J.Mol.CellCardiol.* 23, 187–197 (1991) and van Krimpen et al. *J. Mol. CellCardiol.* 23 1245–1253 (1991) and also Smits et al., *Journal of Cardiovascular Pharmacology*, 20:772–778 (1992). In both techniques, a cardiac infarction is induced in rats in the rat model, and the active ingredient is administered over weeks after the infarction, for example using an osmotic minipump. The active ingredients are advantageously administered from three to five weeks after the myocardial infarction has been induced, and the haemodynamic effects as well as the formation of the relevant DNA are ascertained. The results clearly show that on the one hand the DNA synthesis is significantly reduced and on the other hand the negative haemodynamic effects are normalised. Corresponding animal experiment results with the ACE-inhibitor captopril, known to be used in the treatment of post myocardial infarction, could be confirmed with captopril also in humans [Pfeffer et al. *N.Engl.J.Med.* 1992, 327, 669–677].

Altogether, the compounds according to the invention and the salts thereof are therefore distinguished by a favourable profile of activity.

Accordingly, the compounds of formula I and the pharmaceutically acceptable salts thereof may be used, for example, as active ingredients that are employed, for example, in the treatment of disorders caused by modulation of the $AT_2$-receptor, for example in the treatment of disorders of the kind described hereinbefore. The invention thus relates to the use of compounds of formula I and pharmaceutically acceptable salts thereof in the preparation of corresponding medicaments and in the therapeutic treatment of disorders caused by modulation of the $AT_2$-receptor. Also included in the preparation of the medicaments is the commercial presentation of the active substances.

The compounds of formula I may be in the form of salts, especially pharmaceutically acceptable salts. If the compounds I have, for example, at least one basic centre, they can form acid addition salts. Those salts are formed, for example, with strong inorganic acids, such as mineral acids, e.g. sulfuric acid, a phosphoric acid or a hydrohalic acid, with strong organic carboxylic acids, such as unsubstituted or substituted, e.g. halosubstituted, $C_1$-$C_4$alkanecarboxylic acids, e.g. acetic acid, saturated or unsaturated dicarboxylic acids, e.g. oxalic, malonic, succinic, maleic, fumaric, phthalic or terephthalic acid, hydroxycarboxylic acids, e.g. ascorbic, glycolic, lactic, malic, tartaric or citric acid, amino acids, e.g. aspartic or glutamic acid, or benzoic acid, or with organic sulfonic acids, such as unsubstituted or substituted, e.g. halosubstituted, $C_1$-$C_4$alkane- or aryl-sulfonic acids, e.g. methane- or p-toluene-sulfonic acid. Corresponding acid addition salts may also be formed with a basic centre optionally present in addition. Also, compounds I having at least one acid group (e.g. COOH or 5-tetrazolyl) can form salts with bases. Suitable salts with bases are, for example, metal salts, such as alkali metal or alkaline earth metal salts, e.g. sodium, potassium or magnesium salts, or salts with ammonia or an organic amine, such as morpholine, thiomorpholine, piperidine, pyrrolidine, a mono-, di- or tri-lower alkylamine, e.g. ethyl-, tert-butyl-, diethyl-, diisopropyl-, triethyl-, tributyl- or dimethyl-propyl-amine, or a mono-, di- or tri-hydroxy-lower alkylamine, e.g. mono-, di- or tri-ethanolamine. Furthermore, corresponding internal salts may be formed. Also included are salts that are not suitable for pharmaceutical use, which are used, for example, for the isolation or purification of free compounds I or pharmaceutically acceptable salts thereof.

The compounds according to the invention have at least two optically active carbon atoms and may accordingly be in the form of stereoisomers or mixtures of stereoisomers or in the form of pure enantiomers or diastereoisomers. The present invention also includes corresponding stereoisomers. Aryl and aryl, for example, in aryl-lower alkyl, aryl-lower alkoxy-lower alkyl, aryl-lower alkoxycarbonyl or aryloxycarbonyl and also in aryl-lower alkanoyl, is preferably carbocyclic aryl, such as phenyl or naphthyl, or heterocyclic aryl, such as monocyclic monoaza-, monooxa-, monothia-, diaza-, oxaza- or thiaza-aryl, e.g. pyrrolyl, pyridyl, furyl, thienyl, imidazolyl, isoxazolyl, or thiazolyl. Such carbocyclic and heterocyclic aryl radicals are, for example, independently of one another, unsubstituted or mono- or poly-substituted, e.g. di- or tri-substituted, by substituents selected from the group consisting of: lower alkyl, aryl-lower alkyl, lower alkoxy-lower alkyl, lower alkoxy, lower alkoxy-lower alkoxy, aryl-lower alkoxy, $C_3$-$C_7$cycloalkyl, $C_3$-$C_7$cycloalkyl-lower alkyl, nitro, halogen, trifluoromethyl, amino and amino that is monosubstituted or disubstituted, the substituents being independent of one another, by lower alkyl, aryl-lower alkyl or by aryl, or disubstituted by lower alkylene or by lower alkyleneoxy-lower alkylene. Preferred aryl is phenyl that is unsubstituted or mono- or poly-substituted, e.g. di- or tri-substituted, in the manner indicated hereinbefore.

Acyl is, for example, lower alkanoyl, aryl-lower alkanoyl, or aroyl, especially benzoyl, that may be unsubstituted or may be substituted as indicated hereinbefore for carbocyclic aryl.

The general terms used hereinbefore and hereinafter have the following meanings, unless specified to the contrary:

The term "lower" denotes that corresponding groups and compounds each contain especially up to and including 7, preferably up to and including 4, carbon atoms.

Lower alkyl ist especially $C_1$-$C_7$alkyl, that is methyl, ethyl, n-propyl, isopropyl, n-butyl, isobutyl, sec-butyl, tert-butyl or a corresponding pentyl, hexyl or heptyl radical. $C_1$-$C_4$alkyl is preferred.

Lower alkenyl is especially $C_3$-$C_7$alkenyl and is e.g. 2-propenyl or 1-, 2- or 3-butenyl. $C_3$-$C_5$alkenyl is preferred.

Lower alkynyl is especially $C_3$-$C_7$alkynyl and is preferably propargyl.

Hydroxy-lower alkyl is especially hydroxy-$C_1$-$C_4$alkyl, such as hydroxymethyl, 2-hydroxyethyl or 3-hydroxypropyl.

$C_1$-$C_2$alkylene is methylene or 1,1-ethylene or 1,2-ethylene.

$C_3$-$C_7$cycloalkyl is especially cyclopropyl, cyclobutyl, cyclopentyl, cyclohexyl or cycloheptyl. Cyclopentyl and cyclohexyl are preferred.

$C_3$-$C_7$cycloalkyl-lower alkyl is especially $C_3$-$C_7$cycloalkyl-$C_1$-$C_7$alkyl, such as cyclopropylmethyl, 2-cyclopropyl-ethyl, 3-cyclopropyl-propyl, cyclopentyl-methyl, 2-cyclopentyl-ethyl, 3-cyclopentyl-propyl, cyclohexylmethyl, 2-cyclohexyl-ethyl or 3-cyclohexyl-propyl. $C_5$-$C_6$cycloalkyl-$C_1$-$C_4$alkyl, such as cyclohexylmethyl or 2-cyclohexyl-ethyl, is preferred.

Lower alkoxy is especially $C_1$-$C_7$alkoxy, that is methoxy, ethoxy, n-propoxy, isopropoxy, n-butoxy, isobutoxy, sec-butoxy, tert-butoxy or corresponding pentyloxy, hexyloxy or heptyloxy. $C_1$-$C_4$alkoxy is preferred.

Lower alkoxy-lower alkyl is especially $C_1$-$C_4$alkoxy-$C_1$-$C_4$-alkyl, such as 2-methoxyethyl, 2-ethoxyethyl, 2-(n-propyl)-ethyl or ethoxymethyl.

Lower alkoxy-lower alkoxy is especially $C_1$-$C_4$alkoxy-$C_1$-$C_4$-alkoxy, such as methoxymethoxy, ethoxymethoxy, 2-methoxy-ethoxy or 2-ethoxy—ethoxy.

Halogen is especially halogen having an atomic number of up to and including 35, that is fluorine, chlorine or bromine and also includes iodine.

Lower alkylene is especially $C_2$-$C_7$alkylene, is straight-chain or branched and is especially ethylene, 1,3-propylene, 1,4-butylene, 1,2-propylene, 2-methyl-1,3-propylene or 2,2-dimethyl-1,3-propylene. $C_2$-$C_5$alkylene is preferred.

Lower alkyleneoxy-lower alkylene is especially $C_2$-$C_4$alkylene-oxy-$C_2$-$C_4$alkylene, preferably ethyleneoxy-ethylene.

Lower alkoxycarbonyl is especially $C_2$-$C_8$alkoxycarbonyl and is e.g. methoxy-, ethoxy-, propoxy- or pivaloyloxy-carbonyl. $C_2$-$C_5$alkoxycarbonyl is preferred.

Lower alkoxy-lower alkoxycarbonyl is especially $C_1$-$C_4$alkoxy-$C_1$-$C_4$alkoxycarbonyl, preferably ethoxyethoxycarbonyl, methoxyethoxycarbonyl or isopropoxyethoxycarbonyl.

Naphthyl is especially 1- or 2-naphthyl.

Pyrrolyl is especially 2- or 3-pyrrolyl.

Pyridyl is especially 2-, 3- or 4-pyridyl.

Furyl is especially 2- or 3-furyl.

Thienyl is especially 2- or 3-thienyl.

Imidazolyl is especially 2-, 4- or 5-imidazolyl.

Isoxazolyl is especially 3- or 4-isoxazolyl.

Thiazolyl is especially 2-, 3- or 5-thiazolyl.

Lower alkanoyl is especially $C_1$-$C_7$alkanoyl and is e.g. formyl, acetyl, propionyl, butyryl, isobutyryl or pivaloyl. $C_2$-$C_5$alkanoyl is preferred.

Phenyl-lower alkanoyl is especially phenyl-$C_2$-$C_5$alkanoyl and is e.g. phenylacetyl, 3-phenylpropionyl or 4-phenylbutyryl.

Lower alkylamino is especially $C_1$-$C_7$alkylamino and is e.g. methyl-, ethyl-, n-propyl- or isopropyl-amino. $C_1$-$C_4$alkylamino is preferred.

Phenyl-lower alkylamino is preferably phenyl-$C_1$-$C_4$alkylamino, especially benzyl- or 1- or 2-phenylethyl-amino.

Di-lower alkylamino is especially di-$C_1$-$C_4$alkylamino, such as dimethyl-, diethyl-, di(n-propyl)-, methyl-propyl-, methyl-ethyl-, methyl-butyl- or dibutyl-amino.

N-lower alkyl-N-phenyl-lower alkyl-amino is especially N-$C_1$-$C_4$alkyl-N-phenyl-$C_1$-$C_4$alkyl-amino, preferably methyl-benzyl-amino or ethyl-benzyl-amino.

Di(phenyl-lower alkyl)amino is especially di(phenyl-$C_1$-$C_4$alkyl)amino, preferably dibenzylamino.

Amino that is disubstituted by lower alkylene is especially $C_2$-$C_6$alkyleneamino, preferably $C_4$-$C_6$alkyleneamino, such as 1-pyrrolidino or 1-piperidino.

Amino that is disubstituted by lower alkyleneoxy-lower alkylene is especially $C_2$-$C_4$alkyleneoxy-$C_2$-$C_4$alkyleneamino, preferably 4-morpholino.

Halo-lower alkanesulfonyl is especially halo-$C_1$-$C_7$alkanesulfonyl, such as chloromethane-, fluoro-dichloromethane-, trichloromethane- or trifluoromethane-sulfonyl. Halo-$C_1$-$C_4$alkanesulfonyl is preferred.

The invention relates especially to compounds of formula I wherein

Ar is aryl;

X is —O— or —S(O)$_n$— and n is 0, 1 or 2;

$X_1$ is $C_1$-$C_2$alkylene or a direct bond;

$R_1$ is hydrogen, lower alkyl, aryl-lower alkyl or acyl;

$R_2$ is lower alkyl, aryl-lower alkyl or $C_3$-$C_7$cycloalkyl-lower alkyl;

$R_3$ is carboxy, lower alkoxycarbonyl, lower alkoxy-lower alkoxycarbonyl, aryl-lower alkoxycarbonyl or aryloxycarbonyl;

the ring A and aromatic radicals are, independently of one another, unsubstituted or mono- or poly-substituted by substituents selected from the group consisting of: lower alkyl, aryl-lower alkyl, lower alkoxy-lower alkyl, lower alkoxy, lower alkoxy-lower alkoxy, aryl-lower alkoxy, $C_3$-$C_7$cycloalkyl, $C_3$-$C_7$cycloalkyl-lower alkyl, nitro, halogen, trifluoromethyl, amino and amino that is monosubstituted or disubstituted, the substituents being independent of one another, by lower alkyl, aryl-lower alkyl or by aryl, or disubstituted by lower alkylene or by lower alkyleneoxy-lower alkylene;

or salts thereof.

The invention relates especially to compounds of formula I wherein

Ar is phenyl;

X is —O— or —S(O)$_n$— and n is 0, 1 or 2;

$X_1$ is $C_1$-$C_2$alkylene or a direct bond;

$R_1$ is hydrogen, lower alkyl, lower alkyl that is substituted by phenyl, naphthyl, pyrrolyl, pyridyl, furyl, thienyl, imidazolyl, isoxazolyl or by thiazolyl, lower alkanoyl, lower alkanoyl that is substituted by phenyl, naphthyl, pyrrolyl, pyridyl, furyl, thienyl, imidazolyl, isoxazolyl or by thiazolyl, or benzoyl;

$R_2$ is (i) lower alkyl, lower alkyl that is substituted by phenyl, naphthyl, pyrrolyl, pyridyl, furyl, thienyl, imidazolyl, isoxazolyl or by thiazolyl, or $C_3$-$C_7$cycloalkyl-lower alkyl, or (ii) hydroxy-lower alkyl, lower alkoxy-lower alkyl, or lower alkoxy-lower alkyl in which the lower alkoxy moiety is substituted by phenyl, naphthyl, pyrrolyl, pyridyl furyl, thienyl, imidazolyl, isoxazolyl or by thiazolyl;

$R_3$ is (i) carboxy, 5-tetrazolyl, $PO_2H_2$, $PO_3H_2$ or $SO_3H_2$ or (ii) lower alkoxycarbonyl, lower alkoxy-lower alkoxycarbonyl phenyl-lower alkoxycarbonyl, benzoylcarbonyl, carbamoyl, lower alkylcarbamoyl, di-lower alkylcarbamoyl, phenyl-lower alkylcarbamoyl, diphenyl-lower alkylcarbamoyl, hydroxycarbamoyl, lower alkanesulfonyl-carbamoyl, halo-lower alkanesulfonyl or phenylsulfonyl;

the ring A and carbocyclic and heterocyclic aromatic radicals are, independently of one another, unsubstituted or mono- or poly-substituted by substituents selected from the group consisting of: lower alkyl, lower alkyl that is substituted by phenyl, naphthyl, pyrrolyl, pyridyl, furyl, thienyl, imidazolyl, isoxazolyl or by thiazolyl, lower alkoxy-lower alkyl, lower alkoxy, lower alkoxy-lower alkoxy, phenyl-lower alkoxy, $C_3$-$C_7$cycloalkyl, $C_3$-$C_7$cycloalkyl-lower alkyl, nitro, halogen, trifluoromethyl, amino and amino that is monosubstituted or disubstituted, the substituents being independent of one another, by lower alkyl, phenyl-lower alkyl or by phenyl, or disubstituted by lower alkylene or by lower alkyleneoxy-lower alkylene;

or salts thereof.

The invention relates especially to compounds of formula I wherein

Ar is phenyl;

X is —O— or —S(O)$_n$— and n is 0, 1 or 2;

$X_1$ is $C_1$-$C_2$alkylene or a direct bond;

$R_1$ is hydrogen, lower alkyl, phenyl-lower alkyl, lower alkanoyl, phenyl-lower alkanoyl or benzoyl;

$R_2$ is lower alkyl, phenyl-lower alkyl or $C_3$-$C_7$cycloalkyl-lower alkyl;

$R_3$ is (i) carboxy, 5-tetrazolyl, $PO_2H_2$, $PO_3H_2$ or $SO_3H_2$ or (ii) carbamoyl or hydroxy-carbamoyl;

the ring A and carbocyclic and heterocyclic aromatic radical are, independently of one another, unsubstituted or mono- or poly-substituted by substituents selected from the group consisting of: lower alkyl, phenyl-lower alkyl, lower alkoxy-lower alkyl, lower alkoxy, lower alkoxy-lower alkoxy, phenyl-lower alkoxy, $C_3$-$C_7$cycloalkyl, $C_3$-$C_7$cycloalkyl-lower alkyl, nitro, halogen, trifluoromethyl, amino and amino that is monosubstituted or disubstituted, the substituents being independent of one another, by lower alkyl, phenyl-lower alkyl or by phenyl, or disubstituted by lower alkylene or by lower alkyleneoxy-lower alkylene;

or salts thereof.

The invention relates especially to compounds of formula I wherein

Ar is phenyl or phenyl substituted by $C_1$-$C_4$alkyl;

X is —O— or —S(O)$_n$— and n is 0, 1 or 2;

$X_1$ is $C_1$-$C_2$alkylene or a direct bond;

$R_1$ is hydrogen, $C_1$-$C_4$alkyl or $C_2$-$C_5$alkanoyl;

$R_2$ is phenyl-$C_1$-$C_4$alkyl wherein phenyl is unsubstituted or is substituted by halogen, trifluoromethyl, $C_1$-$C_4$alkyl or by $C_1$-$C_4$alkoxy, or $R_2$ is $C_3$-$C_7$cycloalkyl-$C_1$-$C_4$alkyl;

$R_3$ is carboxy, 5-tetrazolyl, $PO_2H_2$, $PO_3H_2$ or $SO_3H_2$;

the ring A is unsubstituted or mono- or poly-substituted by substituents selected from the group consisting of: $C_1$-$C_4$alkyl, halogen, $C_1$-$C_4$alkoxy-$C_1$-$C_4$alkyl, $C_1$-$C_4$alkoxy, $C_1$-$C_4$alkoxy-$C_1$-$C_4$alkoxy, nitro, halogen and trifluoromethyl;

or salts thereof.

The invention relates especially to compounds of formula I wherein

Ar is phenyl substituted by $C_1$-$C_4$alkyl, lower alkoxy, halogen, trifluoromethyl, amino, lower alkylamino, di-lower alkylamino or by nitro;

X is —O—;

$X_1$ is methylene;

$R_1$ is hydrogen or $C_2$-$C_5$alkanoyl;

$R_2$ is phenyl-$C_1$-$C_4$alkyl wherein phenyl is unsubstituted or is substituted by halogen, trifluoromethyl, $C_1$-$C_4$alkyl or by $C_1$-$C_4$alkoxy; or $R_2$ is $C_3$-$C_7$cycloalkyl-$C_1$-$C_4$alkyl;

$R_3$ is carboxy, carbamoyl or hydroxycarbamoyl;

the ring A is unsubstituted or mono- or poly-substituted by substituents selected from the group consisting of: $C_1$-$C_4$alkyl, halogen, $C_1$-$C_4$alkoxy-$C_1$-$C_4$alkyl, $C_1$-$C_4$alkoxy, $C_1$-$C_4$alkoxy-$C_1$-$C_4$alkoxy, nitro, halogen and trifluoromethyl;

or salts thereof.

The invention relates especially to compounds of formula I wherein

Ar is phenyl or phenyl substituted, especially in the para-position, by $C_1$-$C_4$alkyl, such as p-isopropylphenyl;

X is —O—;

$X_1$ is methylene;

$R_1$ is hydrogen or $C_2$-$C_5$alkanoyl;

$R_2$ is phenyl-$C_1$-$C_4$alkyl wherein phenyl is unsubstituted or is substituted by halogen, trifluoromethyl, $C_1$-$C_4$alkyl or by $C_1$-$C_4$alkoxy; or $R_2$ is $C_3$-$C_7$cycloalkyl-$C_1$-$C_4$alkyl;

$R_3$ is carboxy or 5-tetrazolyl;

the ring A is unsubstituted or is mono- or poly-substituted by substituents selected from the group consisting of: $C_1$-$C_4$alkyl, halogen, $C_1$-$C_4$alkoxy-$C_1$-$C_4$alkyl, $C_1$-$C_4$alkoxy, $C_1$-$C_4$alkoxy-$C_1$-$C_4$alkoxy, nitro, halogen and trifluoromethyl;

or salts thereof.

The invention relates especially to compounds of formula (Ia)

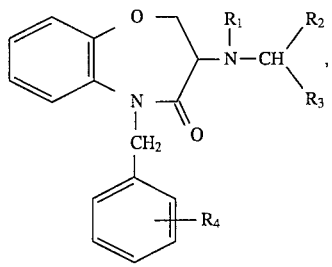

wherein $R_1$ is hydrogen;

$R_2$ is phenyl-$C_1$-$C_4$alkyl, such as benzyl, wherein phenyl is unsubstituted or is substituted by halogen, such as fluorine, trifluoromethyl, $C_1$-$C_4$alkyl, such as methyl, or by $C_1$-$C_4$alkoxy, such as methoxy, or $R_2$ is $C_5$-$C_6$cycloalkyl- $C_1$-$C_4$alkyl, such as cyclohexylmethyl or 2-cyclohexyl-ethyl;

$R_3$ is carboxy; and $R_4$ is $C_1$-$C_4$alkyl, especially isopropyl, that is bonded especially in the para-position;

or salts thereof.

The invention relates especially to compounds of formula (Ib)

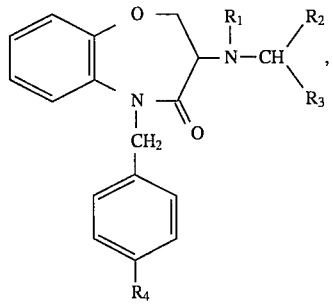

wherein $R_1$ is hydrogen;

$R_2$ is phenyl-$C_1$-$C_4$alkyl, such as benzyl, or $C_5$-$C_6$cycloalkyl-$C_1$-$C_4$alkyl, such as cyclohexylmethyl or 2-cyclohexyl-ethyl;

$R_3$ is carboxy; and $R_4$ is $C_1$-$C_4$alkyl, especially isopropyl;

or salts thereof.

The invention relates to compounds of formulae I, Ia and Ib wherein the carbon atom having the variables $R_2$ and $R_3$ has the (S)-configuration. Preferred are compounds of formulae I, Ia and Ib wherein both the carbon atom having the variables $R_2$ and $R_3$, and the heterocycle carbon atom to which the amino group is bonded, have the (S)-configuration.

The invention relates specifically to the novel compounds of formula I mentioned in the Examples and to the stereoisomers and salts thereof.

The invention relates furthermore to a process for the preparation of compounds of formula I and the stereoisomers and salts thereof, which comprises, for example, a) in a compound of formula

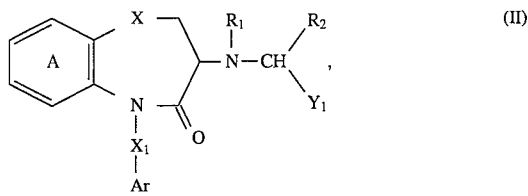

wherein $Y_1$ is a radical that can be converted into the variable $R_3$, or in a salt thereof, converting $Y_1$ into the variable $R_3$; or, b) for the preparation of a compound of formula (I) wherein $R_1$ is hydrogen, or for the preparation of a salt thereof, in a compound of formula

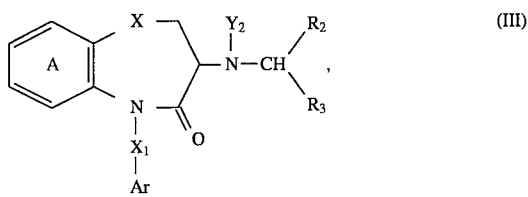

wherein $Y_2$ is an amino-protecting group, or in a salt thereof, removing the amino-protecting group; or c) reacting a compound of formula

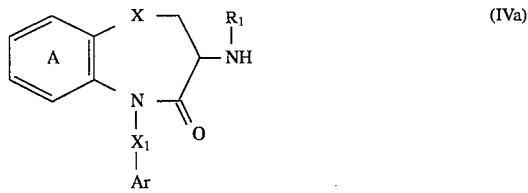

with a compound of formula

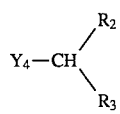

(IVb), wherein $Y_4$ is a nucleofugal leaving group, or with a compound of formula $R_2$—CO—$R_3$ (IVc) or a salt thereof; or d) reacting a compound of formula

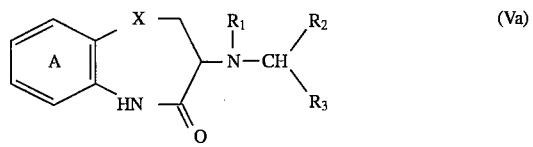

with a compound of formula $Y_6$—$X_1$—Ar (Vb), wherein $Y_6$ is a nucleofugal leaving group, or with a salt thereof; or c) reacting a compound of formula

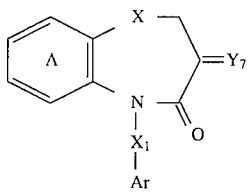

wherein $Y_7$ is (i) oxo or (ii) reactive esterified hydroxy together with hydrogen, with a compound of formula

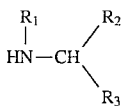

(VIb) or with a salt thereof;
and in each case, if desired, isolating in free form or in salt form a compound of formula I obtainable according to the process or in some other manner, converting a compound of formula I obtainable according to the process or in some other manner into a different compound of formula I, separating a mixture of isomers obtainable according to the process and isolating the desired isomer and/or converting a free compound of formula I obtainable according to the process into a salt or converting a salt of a compound of formula I obtainable according to the process into the free compound of formula I or into a different salt.

The reactions described in the variants hereinbefore and hereinafter are carried out in a manner known per se, e.g. in the absence or customarily in the presence of a suitable solvent or diluent or a mixture thereof, if required with cooling, at room temperature or with heating, e.g. in a temperature range of approximately from −80° C. to the boiling temperature of the reaction medium, preferably from approximately −10° to approximately +200° C., and, if necessary, in a closed vessel, under pressure, in an inert gas atmosphere and/or under anhydrous conditions.

Details concerning corresponding procedures and reaction conditions may be found especially also in the Examples.

Variant a):

A radical $Y_1$ that can be converted into carboxy $R_3$ is, for example, functionally modified carboxy or a radical that can be converted oxidatively into carboxy.

There comes into consideration as functionally modified carboxy, for example, esterified carboxy different from $R_3$, amidated carboxy or cyano.

Esterified carboxy different from $R_3$ is, for example, carboxy esterified by an unsubstituted or substituted aliphatic, cycloaliphatic or aromatic alcohol. An aliphatic alcohol is, for example, a lower alkanol, such as methanol, ethanol, n-propanol, isopropanol, n-butanol, sec-butanol or tert-butanol, that is substituted by cyano or by a silyl radical, while there comes into consideration as a cycloaliphatic alcohol, for example, a 3- to 8-membered cycloalkanol, such as cyclo-pentanol, -hexanol or -heptanol. An aromatic alcohol is, for example, a phenol or a heterocyclic alcohol, each of which may be substituted, especially hydroxypyridine, e.g. 2-, 3- or 4-hydroxypyridine.

Amidated carboxy is, for example, carbamoyl, or carbamoyl that is monosubstituted by hydroxy, amino or by unsubstituted or substituted phenyl, mono- or di-substituted by lower alkyl, or disubstituted by 4- to 7-membered alkylene or by 3-aza-, 3-lower alkylaza-, 3-oxa- or 3-thia-alkylene. There may be mentioned as examples carbamoyl, N-mono- or N,N-di-lower alkylcarbamoyl, such as N-methyl-, N-ethyl-, N,N-di-methyl-, N,N-diethyl- and N,N-dipropyl-carbamoyl, pyrrolidino- and piperidino-carbonyl, morpholino-, piperazino-, 4-methylpiperazino- and thiomorpholino-carbonyl, anilinocarbonyl and anilinocarbonyl substituted by lower alkyl, lower alkoxy and/or by halogen.

Preferred functionally modified carboxy is, for example, cyano-lower alkoxycarbonyl, such as 2-cyanoethoxycarbonyl, silyloxy-carbonyl, such as tri-lower alkylsilyloxycarbonyl, e.g. tri(m)ethylsilyloxycarbonyl, and cyano.

Preferred $Y_1$ is, for example, cyano.

Compounds of formula I wherein $R_3$ is carboxy may be prepared, for example, starting from compounds of formula II wherein $Y_1$ is cyano, esterified carboxy different from $R_3$, or amidated carboxy, by means of hydrolysis, especially in the presence of a base.

The following $Y_1$ especially can be converted in a manner known per se into carboxy $R_3$: 2-cyanoethoxycarbonyl $Y_1$ can be converted into carboxy $R_3$, for example, by means of hydrolysis in the presence of a base, 2-trimethylsilyloxycarbonyl can be converted into carboxy $R_3$ by treatment with a fluoride, such as an alkali metal fluoride, e.g. sodium fluoride, and silyloxycarbonyl $Y_1$ can be converted into carboxy $R_3$ by treatment with an acid.

There come into consideration as bases, for example, alkali metal hydroxides, hydrides, amides, alkanolates, carbonates, triphenylmethylides, di-lower alkylamides, aminoalkylamides or lower alkylsilylamides, naphthaleneamines, lower alkylamines, basic heterocycles, ammonium hydroxides, as well as carbocyclic amines. There may be mentioned by way of example sodium hydroxide, hydride and amide, potassium tert-butanolate, potassium carbonate, lithium triphenylmethylide, lithium diisopropylamide, potassium 3-(aminopropyl)-amide, potassium bis-(trimethylsilyl)-amide, dimethylaminonaphthalene, di- or tri-ethylamine, or ethyl-diisopropylamine, N-methylpiperidine, pyridine, benzyltrimethylammonium hydroxide, 1,5-diazabicyclo[4.3.0]non-5-ene (DBN) and also 1,8-diazabicyclo[5.4.0]undec-7-ene (DBU).

There comes into consideration as an acid, for example, a strong inorganic acid, such as a mineral acid, e.g. sulfuric acid, a phosphoric acid or a hydrohalic acid, a strong organic carboxylic acid, such as an unsubstituted or substituted, e.g. halosubstituted, $C_1$-$C_4$alkanecarboxylic acid, e.g. acetic or trifluoroacetic acid, or an organic sulfonic acid, such as an unsubstituted or substituted, e.g. halosubstituted, $C_1$-$C_4$alkane- or aryl-sulfonic acid, e.g. methane- or p-toluene-sulfonic acid.

There comes into consideration as a radical that can be converted oxidatively into carboxy, for example, hydroxymethyl, or formyl optionally formed in situ.

Starting from compounds of formula II wherein $Y_1$ is hydroxymethyl or formyl, carboxy $R_3$ can be produced by means of oxidation. The oxidation is carried out, for example, in an inert solvent, such as in a lower alkanecarboxylic acid, e.g. acetic acid, a ketone, e.g. acetone, an ether, e.g. tetrahydrofuran, a heterocyclic aromatic compound, e.g. pyridine, or in water, or in a mixture thereof, if necessary with cooling or heating, e.g. in a temperature range of from approximately 0° to approximately +150° C. There come into consideration as oxidizing agents, for example, oxidizing transition metal compounds, especially those with elements of sub-group I, VI or VII. There may be mentioned as examples: silver compounds, such as silver nitrate, oxide and picolinate, chromium compounds, such as chromium trioxide and potassium dichromate, and manganese compounds, such as potassium, tetrabutylammonium and benzyltriethylammonium permanganate. Other oxidizing agents are, for example, suitable compounds with elements of main group IV, such as lead dioxide, or halogen/oxygen compounds, such as sodium iodate or potassium periodate.

A radical $Y_1$ that can be converted into 5-tetrazolyl $R_3$ is, for example, cyano or N-protected 5-tetrazolyl.

In order to prepare compounds of formula I wherein $R_3$ is 5-tetrazolyl, there is used as starting material, for example, a compound of formula II wherein $Y_1$ is cyano, which is reacted with an azide, for example with $HN_3$ or especially a salt, such as an alkali metal salt, thereof, or with an organotin azide, such as a tri-lower alkyltin or triaryltin azide. Preferred azides are, for example, sodium and potassium azide and also tri-$C_1$-$C_4$alkyl-, e.g. triethyl- or tributyl-tin azide, and triphenyltin azide.

There come into consideration as protecting groups of N-protected 5-tetrazolyl $R_3$ the protecting groups customarily used in tetrazole chemistry, especially triphenylmethyl, unsubstituted or substituted, e.g. nitro-substituted, benzyl, such as 4-nitrobenzyl, lower alkoxymethyl, such as methoxy- or ethoxy-methyl, lower alkylthiomethyl, such as methylthiomethyl, and 2-cyanoethyl, also lower alkoxy-lower alkoxymethyl, such as 2-methoxyethoxymethyl, benzyloxymethyl, and also phenacyl. The removal of the protecting groups is carried out in accordance with known methods, for example as described in J. Green, Protective Groups in Organic Synthesis, Wiley-Interscience (1980). For example triphenylmethyl is customarily removed by hydrolysis, especially in the presence of an acid, or by hydrogenolysis in the presence of a hydrogenation catalyst, 4-nitrobenzyl is removed, for example, by hydrogenolysis in the presence of a hydrogenation catalyst, methoxy- or ethoxy-methyl is removed, for example, by treatment with a tri-lower alkyltin bromide, such as triethyl- or tributyl-tin bromide, methylthiomethyl is removed, for example, by treatment with trifluoroacetic acid, 2-cyanoethyl is removed, for example, by hydrolysis, for example with sodium hydroxide solution, 2-methoxyethoxymethyl is removed, for example, by hydrolysis, e.g. with hydrochloric acid, and benzyloxymethyl and phenacyl are removed, for example, by hydrogenolysis in the presence of a hydrogenation catalyst.

A radical $Y_1$ that can be converted into $PO_2H_2$ or $PO_3H_2$ $R_3$ is, for example, a functional derivative of $PO_2H_2$ or $PO_3H_2$ respectively.

A corresponding radical $Y_1$ that can be converted into $R_3$ is, for example, a group $-N_2^+ A^-$, wherein $A^-$ is an anion of an acid, such as a mineral acid. Corresponding diazonium compounds are, for example, reacted in a manner known per se with a P(III) halide, such as $PCl_3$ or $PBr_3$, and worked up hydrolytically, compounds of formula I wherein $R_3$ is $PO_3H_2$ being obtainable.

A radical $Y_1$ that can be converted into $SO_3H$ $R_3$ is, for example, the mercapto group. Starting compounds of formula II containing such a group are oxidized, for example by oxidation processes known per se, to compounds of formula I wherein $R_3$ is $SO_3H$. There come into consideration as oxidizing agents, for example, inorganic peracids, such as peracids of mineral acids, e.g. periodic acid or persulfuric acid, organic peracids, such as percarboxylic or persulfonic acids, e.g. performic, peracetic, trifluoroperacetic or perbenzoic acid or p-toluenepersulfonic acid, or mixtures of hydrogen peroxide and acids, e.g. mixtures of hydrogen peroxide and acetic acid. Frequently the oxidation is carried out in the presence of suitable catalysts. There may be mentioned as catalysts suitable acids, such as unsubstituted or substituted carboxylic acids, e.g. acetic acid or trifluoroacetic acid, and transition metal oxides, such as oxides of elements of sub-group VI, e.g. molybdenum oxide or tungsten oxide.

The oxidation is carried out under mild conditions, e.g. at temperatures of from approximately $-50°$ to approximately $+100°$ C.

The starting material of formula II is obtainable, for example, by reacting a compound of formula

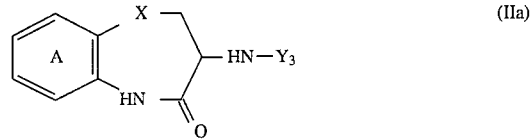

(IIa)

or a salt thereof, wherein $Y_3$ is one of the above-mentioned amino-protecting groups, for example phthaloyl, with a compound of formula

$Ar-X_1-Y_4$ (IIb)

wherein $Y_4$ is reactive esterified hydroxy and $X_1$ is $C_1$-$C_2$alkylene, in the presence of a base. In the next reaction step, the amino-protecting group is removed in a manner known per se, for example the phthaloyl group is removed by treatment with hydrazine hydrate. A compound of formula

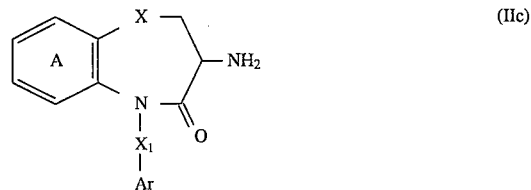

(IIc)

so obtainable is then reacted with a compound of formula

(IId)

wherein $Y_4$ is a nucleofugal leaving group, such as a diazonium radical or reactive esterified hydroxy, in the presence of base, to form a compound of formula II wherein $R_1$ is hydrogen. If desired a corresponding compound may be N-alkylated or N-acylated in a manner known per se to form a compound of formula II.

Reactive esterified hydroxy is especially hydroxy esterified by a strong inorganic acid or organic sulfonic acid, for example halogen, such as chlorine, bromine or iodine, or sulfonyloxy, such as hydroxysulfonyloxy, halosulfonyloxy, e.g. fluorosulfonyloxy, unsubstituted or substituted, e.g. halosubstituted, $C_1$-$C_7$alkanesulfonyloxy, e.g. methane- or trifluoromethane-sulfonyloxy, $C_5$-$C_7$cycloalkanesulfonyloxy, e.g. cyclohexanesulfonyloxy, or unsubstituted or substituted, e.g. $C_1$-$C_7$alkyl- or halosubstituted, benzenesulfonyloxy, e.g. p-bromophenyl- or p-toluene-sulfonyloxy, especially halogen, such as chloride, bromide or iodide, as well as sulfonyloxy, such as methane- or p-toluene-sulfonyloxy.

A specific method of preparing compounds of formula II is described especially in working Example 1.

The starting materials of formulae IIa, IIb and IId are known or can be prepared according to methods known per se.

Variant b):

There come into consideration as the amino-protecting group $Y_2$ the protecting groups customarily used in peptide chemistry, especially triphenylmethyl, unsubstituted or substituted, e.g. nitro-substituted, benzyl, such as 4-nitrobenzyl, lower alkoxymethyl, such as methoxy- or ethoxymethyl, lower alkylthiomethyl, such as methylthiomethyl, and 2-cyanoethyl, also lower alkoxy-lower alkoxymethyl, such as 2-methoxyethoxymethyl, benzyloxymethyl and also phenacyl. The removal of the protecting groups is carried out in accordance with known methods, for example as described in J. Green, Protective Groups in Organic Synthesis, Wiley-Interscience (1980). For example triphenylmethyl is customarily removed by hydrolysis, especially in the presence of an acid, or by hydrogenolysis in the presence of a hydrogenation catalyst, 4-nitrobenzyl is removed, for example, by hydrogenolysis in the presence of a hydrogenation catalyst, methoxy- or ethoxy-methyl is removed, for example, by treatment with a tri-lower alkyltin bromide, such as triethyl- or tributyl-tin bromide, methylthiomethyl is removed, for example, by treatment with trifluoroactic acid, 2-cyanoethyl is removed, for example, by hydrolysis, for example with sodium hydroxide solution, 2-methoxyethoxymethyl is removed, for example, by hydrolysis, e.g. with hydrochloric acid, and benzyloxymethyl and phenacyl are removed, for example, by hydrogenolysis in the presence of a hydrogenation catalyst.

The starting material of formula III is obtainable, for example, by reacting one of the compounds described hereinbefore of formula

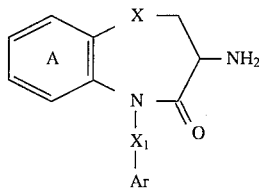

with a compound of formula

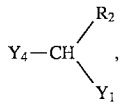

wherein $Y_4$ is a nucleofugal leaving group, such as a diazonium radical or reactive esterified hydroxy, in the presence of a base to form a compound of formula II wherein $R_1$ is hydrogen, and then introducing the aminoprotecting group in a manner known per se.

Variant c):

A nucleofugal leaving group $Y_4$ is, for example, a diazonium radical or is reactive esterified hydroxy as defined hereinbefore. $Y_4$ is advantageously halogen, such as chlorine or bromine, or sulfonyloxy, such as methanesulfonyloxy or 4-nitrophenylsulfonyloxy.

The reaction is carried out in a manner known per se, advantageously in the presence of one of the bases specified hereinbefore.

Some of the starting materials are known, or they can be prepared according to methods known per se.

The preparation of the starting material of formula IVa is carried out, for example, as described in connection with the preparation of compounds of formula III in Variant b).

Variant d):

There comes into consideration as the nucleofugal leaving group $Y_6$ especially reactive esterified hydroxy, which, for example, is as defined hereinbefore.

The reaction is carried out in a manner known per se, advantageously in the presence of one of the bases specified hereinbefore.

The reaction is advantageously carried out with compounds of formula Va wherein $R_3$ is other than carboxy. The reaction is especially advantageously carried out with compounds of formula Va wherein in addition $R_1$ is other than hydrogen.

Some of the starting materials are known, or they can be prepared according to methods known per se.

To prepare a compound of formula (Va), for example a compound of formula IIc is used as starting material and is reacted analogously to Variant c) with a compound of formula IVb or IVc, advantageously in the presence of one of the bases defined hereinbefore.

Variant e):

The reaction is carried out in a manner known per se.

The reductive alkylation ($Y_7$=oxo) is carried out in the presence of customary reducing agents, whereas the substitutive N-alkylation ($Y_7$=reactive esterified hydroxy together with hydrogen) is carried out preferably in the presence of one of the bases defined hereinbefore.

Some of the starting materials are known, or they can be prepared according to methods known per se.

Some of the starting materials used in the above process variants, and the preparation of such materials, are described in U.S. Pat. No. 4,477,464.

A compound of formula I obtainable according to the process or in some other manner may be converted in a manner known per se into a different compound of formula I.

If one of the variables contains amino, corresponding compounds I may be N-(ar)alkylated in a manner known per se; similarly, carbamoyl or radicals containing carbamoyl may be N-(ar)alkylated. The (ar)alkylation is carried out, e.g., with an (aryl-)$C_1$-$C_7$alkyl halide, e.g. bromide or iodide, an (aryl-)$C_1$-$C_7$alkanesulfonate, e.g. methanesulfonate or p-toluenesulfonate, or a di-$C_1$-$C_7$alkyl sulfate, e.g. dimethyl sulfate, preferably under basic conditions, such as in the presence of sodium hydroxide solution or potassium hydroxide solution, and advantageously in the presence of a phase transfer catalyst, such as tetrabutylammonium bromide or benzyltrimethylammonium chloride, in which case, however, more strongly basic condensation agents, such as alkali metal amides, hydrides or alcoholates, e.g. sodium amide, sodium hydride or sodium ethanolate, may be necessary.

A compound of formula I wherein $R_1$ is hydrogen may be acylated in a manner known per se to a compound of formula I wherein $R_1$ is acyl. The reaction is carried out, for example, with a compound of formula $R_1$—OH or a reactive derivative thereof. Reactive derivatives of compounds of formula $R_1$—OH are, for example, reactive anhydrides derived therefrom.

Anhydrides of acids of formula $R_1$—OH may be symmetric or preferably mixed anhydrides of those acids, for example anhydrides with inorganic acids, such as acid halides, especially acid chlorides (obtainable, for example, by treatment of the corresponding acid with thionyl chloride, phosphorus pentachloride or oxalyl chloride; acid chloride method), azides (obtainable, for example, from a corresponding acid ester via the corresponding hydrazide by treatment thereof with nitrous acid; azide method), anhydrides with carbonic acid semiesters, for example carbonic acid lower alkyl semiesters (obtainable, for example, by treatment of the corresponding acid with chloroformic acid lower alkyl esters or with a 1-lower alkoxycarbonyl-2-lower alkoxy-1,2-dihydroquinoline, e.g. 1-ethoxycarbonyl-2-ethoxy-1,2-dihydroquinoline; mixed O-alkylcarbonic acid anhydrides method), anhydrides with dihalogenated, especially dichlorinated, phosphoric acid (obtainable, for example, by treatment of the corresponding acid with phosphorus oxychloride; phosphorus oxychloride method), anhydrides with other phosphoric acid derivatives (for example those obtainable with phenyl-N-phenylphosphoramidochloridate) or with phosphorous acid derivatives, or anhydrides with organic acids, such as mixed anhydrides with organic carboxylic acids (obtainable, for example, by treatment of the corresponding acid with an unsubstituted or substituted lower alkane- or phenyl-lower alkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid with a suitable organic sulfonic acid halide, such as a lower alkane- or aryl-, for example methane- or p-toluene-sulfonic acid chloride; mixed sulfonic acid anhydrides method), as well as symmetric anhydrides (obtainable, for example, by condensation of the corresponding acid in the presence of a carbodiimide or 1-diethylaminopropyne; symmetric anhydrides method).

Condensation to form an amide bond may be carried out in a manner known pew se, for example as described in standard works, such as Houben-Weyl, "Methoden der organischen Chemie", 4th edition, Volume 15/II, Georg Thieme Verlag, Stuttgart 1974, "The Peptides" (editors E. Gross and J. Meienhofer), Volumes 1 and 2, Academic Press, London and New York, 1979/1980, or M. Bodanszky, "Principles of Peptide Synthesis", Springer-Verlag, Berlin 1984.

The condensation may be carried out in the presence of one of the customary condensation agents. Customary condensation agents are, for example, carbodiimides, for example diethyl-, dipropyl-, N-ethyl-N'-(3-dimethylaminopropyl)-carbodiimide or especially dicyclohexylcarbodiimide, also suitable carbonyl compounds, for example carbonyldiimidazole, 1,2-oxazolium compounds, for example 2-ethyl-5-phenyl-1,2-oxazolium 3'-sulfonate and 2-tert-butyl-5-methylisoxazolium perchlorate or a suitable acylamino compound, for example 2-ethoxy-1-ethoxycarbonyl-1,2-dihydroquinoline, and also activated phosphoric acid derivatives, for example diphenylphosphoryl azide, diethylphosphoryl cyanide, phenyl-N-phenylphosphoramidochloridate, bis(2-oxo-3-oxazolidinyl)phosphinic acid chloride or 1-benzotriazolyloxy-tris(dimethylamino)phosphonium hexafluorophosphate.

If desired an organic base is added, for example a tri-lower alkylamine having bulky radicals, such as ethyldiisopropylamine, or a heterocyclic base, for example pyridine, 4-dimethylaminopyridine or preferably N-methylmorpholine.

The condensation of acid anhydrides with amines may be effected, for example, in the presence of inorganic carbonates, for example alkali metal carbonates or hydrogen carbonates, such as sodium or potassium carbonate or hydrogen carbonate (usually together with a sulfate).

The condensation is carried out preferably in an inert, polar, aprotic, preferably anhydrous solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in a mixture thereof, as appropriate at reduced or elevated temperature, for example in a temperature range of from approximately −40° C. to approximately +100° C., preferably from approximately −10° C. to approximately +50° C., and, where appropriate, under an inert gas atmosphere, for example a nitrogen atmosphere.

Reactive acid derivatives may also be formed in situ.

In compounds of formula I that contain an esterified carboxy group as substituent, such a group may be converted into a free carboxy group, for example by means of hydrolysis, for example in the presence of a basic agent or an acid agent, such as a mineral acid. Tert-butoxycarbonyl, for example, may furthermore be converted into carboxy, for example in a manner known per se, such as by treatment with trihaloacetic acid, such as trifluoroacetic acid, advantageously under anhydrous conditions, and benzyloxycarbonyl may be converted into carboxy, for example, by catalytic hydrogenation in the presence of a hydrogenation catalyst, for example in the manner described below.

In addition, in compounds of formula I that have a carboxy group as substituent (especially if $R_3$ is other than carboxy), the carboxy group may be converted, for example by treatment with an alcohol, such as a lower alkanol, in the presence of a suitable esterifying agent, such as an acid reagent, e.g. an inorganic or organic acid or a Lewis acid, e.g. zinc chloride, or a water-binding condensation agent, e.g. a carbodiimide, such as N,N'-dicyclohexylcarbodiimide, or by treatment with a diazo reagent, such as a diazo-lower alkane, e.g. diazomethane, into a correspondingly esterified carboxy group. The latter may also be obtained by treating compounds of formula I wherein the carboxy group is in free form or in the form of a salt, such as an ammonium or metal salt, e.g. an alkali metal salt, such as a sodium or potassium salt, with a $C_1$-$C_7$alkyl halide, e.g. methyl or ethyl bromide or iodide, or with an organic sulfonic acid ester, such as a corresponding $C_1$-$C_7$alkyl ester, e.g. methanesulfonic acid or p-toluenesulfonic acid methyl ester or ethyl ester.

Compounds of formula I that contain an esterified carboxy group as substituent may be converted into different ester compounds of formula I by transesterification, e.g. by treatment with an alcohol, customarily with an alcohol higher than that corresponding to the esterified carboxy group in the starting material, in the presence of a suitable transesterification agent, such as a basic agent, e.g. an alkali metal $C_1$-$C_7$alkanoate, $C_1$-$C_7$alkanolate or cyanide, such as sodium acetate, methanolate, ethanolate, tert-butanolate or cyanide, or of a suitable acid agent, where necessary with removal of the alcohol formed, e.g. by distillation. It is also possible to use as starting material a corresponding so-called activated ester of formula I that contains an activated esterified carboxy group as substituent (see below) and convert that into a different ester by treatment with a $C_1$-$C_7$alkanol.

In compounds of formula I that contain a carboxy group as substituent, this may also first of all be converted into a reactive derivative, such as an anhydride (also a mixed anhydride), an acid halide, e.g. an acid chloride (e.g. by treatment with a thionyl halide, e.g. thionyl chloride), an anhydride with a formic acid ester, e.g. a formic acid $C_1$-$C_7$alkyl ester (e.g. by treatment of a salt, such as an ammonium or alkali metal salt, with a haloformic, such as a chloroformic, acid ester, such as a $C_1$-$C_7$alkyl ester), or an activated ester, such as a cyanomethyl, nitrophenyl, e.g. 4-nitrophenyl, or polyhalophenyl, e.g. pentachlorophenyl, ester (e.g. by treatment with a corresponding hydroxy compound in the presence of a suitable condensation agent, such as N,N'-dicyclohexylcarbodiimide), and such a reactive derivative may then be reacted with a corresponding alcohol component so as to obtain corresponding ester compounds of formula I. Those may be obtained directly or by way of intermediate compounds; for example an activated ester, such as a 4-nitrophenyl ester, of a compound of formula I containing a carboxy group may first of all be reacted with a 1-unsubstituted imidazole and the resulting 1-imidazolylcarbonyl compound may be reacted with a corresponding ester component.

If an aromatic ring contains a hydrogen atom as substituent, then that may be replaced by a halogen atom in customary manner using a halogenating agent, e.g. by bromine using bromine, hypobromic acid, an acylhypobromite or another organic bromine compound, e.g. N-bromosuccinimide, N-bromoacetamide, N-bromophthalimide, pyridinium perbromide, dioxane dibromide, 1,3-dibromo-5,5-dimethylhydantoin or 2,4,4,6-tetrabromo-2,5-cyclohexanedien-1-one, or by chlorine using elemental chlorine, e.g. in a halogenated hydrocarbon, such as chloroform, and with cooling, e.g. to approximately −10° C.

If an aromatic ring contains an amino group, then that may be diazotised in customary manner, e.g. by treatment with a nitrite, e.g. sodium nitrite, in the presence of a suitable protonic acid, e.g. a mineral acid, the reaction temperature advantageously being maintained below approximately 5° C. The diazonium group so obtainable, which is in salt form, may be substituted according to conventional processes, for example as follows: by a hydroxy group analogously to decomposition to phenol in the presence of water; by an alkoxy group by treatment with a corresponding alcohol, for which energy must be supplied; by the fluorine atom analogously to the Schiemann reaction in the thermolysis of corresponding diazonium tetrafluoroborates; or by chlorine, bromine, iodine or the cyano group analogously to the Sandmeyer reaction by reaction with corresponding Cu(I) salts, initially with cooling, e.g. to below approximately 5° C., and then with heating, e.g. to from approximately 60° to approximately 150° C.

The invention relates especially to the processes described in the Examples.

Salts of compounds of formula I may be prepared in a manner known per se. For example acid addition salts of compounds of formula I are obtained by treatment with a suitable acid or a suitable ion exchange reagent. Salts of compounds I may be converted into free compounds I in customary manner, and acid addition salts may be converted into free compounds I e.g. by treatment with a suitable basic agent or a suitable ion exchange reagent.

Salts of compounds I may be converted into different salts of compounds I in a manner known per se.

Depending on the reaction procedure and reaction conditions, compounds I having salt-forming, especially basic, properties, may be obtained in free form or in the form of salts.

Owing to the close relationship between the compounds I in free form and in the form of their salts, hereinbefore and hereinafter any reference to the free compound I and its salts should be understood as including also the corresponding salts and the free compound I, respectively, where appropriate and expedient.

The compounds I, including the salts of salt-forming compounds, may also be obtained in the form of their hydrates and/or may include other solvents, e.g. solvents used for crystallisation.

Depending on the choice of starting materials and procedures, the compounds I and their salts may be in the form of one of the possible isomers or a mixture thereof, for example depending on the number and the absolute and relative configuration of the asymmetric carbon atoms they may be in the form of pure isomers, such as antipodes and/or diastereoisomers, or in the form of mixtures of isomers, such as mixtures of enantiomers, e.g. racemates, mixtures of diastereoisomers or mixtures of racemates.

Resulting mixtures of diastereoisomers and mixtures of racemates can be separated in known manner into the pure diastereoisomers or racemates on the basis of the physicochemical differences between the constituents, for example by fractional crystallisation. Resulting mixtures of enantiomers, such as racemates, may be resolved into the optical antipodes according to known methods, for example by recrystallisation from an optically active solvent, chromatography using chiral adsorbents, by means of suitable microorganisms, by cleavage with specific immobilised enzymes, by the formation of inclusion compounds, e.g. using chiral crown ethers, only one enantiomer being complexed, or by conversion into diastereoisomeric salts, for example by reaction of a basic end-product racemate with an optically active acid, such as a carboxylic acid, for example tartaric acid or malic acid, or sulfonic acid, e.g. camphorsulfonic acid, and separation of the mixture of diastereoisomers obtained in that manner, for example on the basis of their different solubilities, into the diastereoisomers, from which the desired enantiomer can be freed by the action of suitable agents.

The invention relates also to those forms of the process in which a compound obtainable as intermediate at any stage of the process is used as starting material and the remaining steps are carried out, or in which a starting material is used in the form of a derivative or salt and/or its racemates or antipodes or, especially, is formed under the reaction conditions.

The starting materials and intermediates used in the process of the present invention are preferably those which lead to the compounds I described at the beginning as being especially valuable. The invention extends also to novel starting materials and intermediates for the preparation of compounds I, to the use thereof and to a process for the preparation thereof, the variables A, X, $X_1$, $R_1$, $R_2$, $R_3$ and $R_4$ having the meanings given for the compounds I.

The compounds of formula I and the pharmaceutically acceptable salts thereof may be used, preferably in the form of pharmaceutically acceptable compositions, in a method for the prophylactic and/or therapeutic treatment of the animal or human body, especially for the treatment of disorders that are brought about by stimulation or blocking of the $AT_2$-receptor.

The invention therefore also relates to pharmaceutical compositions that comprise as active ingredient a compound I in free form or in the form of a pharmaceutically acceptable salt as well as to a process for the preparation thereof. The pharmaceutical compositions are for enteral, such as oral, or also rectal or parenteral administration to warm-blooded animals, and comprise the pharmacological active ingredient on its own or together with customary pharmaceutical excipients. The pharmaceutical compositions contain e.g. approximately from 0.1% to 100%, preferably from approximately 1% to approximately 60%, active ingredient. Pharmaceutical compositions for enteral and parenteral administration are e.g. in unit dose forms, such as dragées, tablets, capsules or suppositories, and also ampoules. They are prepared in a manner known per se, e.g. by means of conventional mixing, granulating, confectioning, dissolving or lyophilising processes. For example, pharmaceutical compositions for oral administration can be obtained by combining the active ingredient with solid carriers, if desired granulating a resulting mixture, and processing the mixture or granules, if desired or necessary after the addition of appropriate excipients, to form tablets or dragée cores.

Suitable carriers are especially fillers, such as sugars, e.g. lactose, saccharose, mannitol or sorbitol, cellulose preparations and/or calcium phosphates, e.g. tricalcium phosphate or calcium hydrogen phosphate, and binders, such as starch pastes, using e.g. corn, wheat, rice or potato starch, gelatin, gum tragacanth, methylcellulose and/or polyvinylpyrrolidone, and, if desired, disintegrators, such as the abovementioned starches, also carboxymethyl starch, cross-linked polyvinylpyrrolidone, agar or alginic acid or a salt thereof, such as sodium alginate. Excipients are especially flow conditioners and lubricants, e.g. silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/ or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragée coatings, e.g. for identification purposes or to indicate different doses of active ingredient.

Other orally administrable pharmaceutical compositions are dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as lactose, binders, such as starches, and/or glidants, such as talc or magnesium stearate, and, if desired, stabilisers. In soft capsules, the active ingredient is preferably dissolved or suspended in suitable liquids, such as fatty oils, paraffin oil or liquid polyethylene glycols, to which stabilisers may also be added.

There come into consideration as rectally administrable pharmaceutical compositions e.g. suppositories that consist of a combination of the active ingredient with a suppository base. Suitable suppository bases are e.g. natural or synthetic triglycerides, paraffin hydrocarbons, polyethylene glycols and higher alkanols. It is also possible to use gelatin rectal capsules, which contain a combination of the active ingredient with a base material. There come into consideration as base materials e.g. liquid triglycerides, polyethylene glycols and paraffin hydrocarbons.

There are suitable for parenteral administration especially aqueous solutions of an active ingredient in water-soluble form, e.g. in the form of a water-soluble salt, or also suspensions of the active ingredient, such as corresponding oily injection suspensions, there being used suitable lipophilic solvents or vehicles, such as fatty oils, e.g. sesame oil, or synthetic fatty acid esters, e.g. ethyl oleate or triglycerides, or aqueous injection suspensions that comprise viscosity-increasing substances, e.g. sodium carboxymethyl-cellulose, sorbitol and/or dextran, and, if desired, also stabilisers.

The dosage of the active ingredient may depend on various factors, such as mode of administration, species of warm-blooded animal, age and/or individual condition. For a patient weighing approximately 75 kg, the estimated approximate daily dose in the case of oral administration is normally from approximately 10 mg to approximately 2250 mg, especially from approximately 10 mg to approximately 250 mg.

The following Examples illustrate the invention described above; they are not, however, intended to limit the scope thereof in any way. Temperatures are quoted in degrees Celsius (° C).

EXAMPLE 1

3-(S)-[(1-(S)-Carboxy-3-cyclohexylpropyl)amino]-5-(p-isopropylbenzyl)-4-oxo-2,3,4,5-tetrahydro-1,5-benzoxazepine 1.5 g of 3-(S)-[(S)-1-ethoxycarbonyl-3-cyclohexyl-propyl)amino]-5-(p-isopropylbenzyl)-4-oxo-2,3,4,5-tetrahydro-1,5-benzoxazepine are dissolved in 36 ml of methanol, 5 ml of 2N aqueous sodium hydroxide solution are added and the mixture is stirred for 6 hours at room temperature. The reaction mixture is acidified with 1N hydrochloric acid and extracted twice with ethyl acetate and the organic phases are washed twice with water. The combined ethyl acetate phases are dried over sodium sulfate and concentrated by evaporation. The residue is taken up in a small amount of ether and crystallises spontaneously. The material is filtered off and dried overnight at 80° C. under a high vacuum. M.p. 120°–122° C.

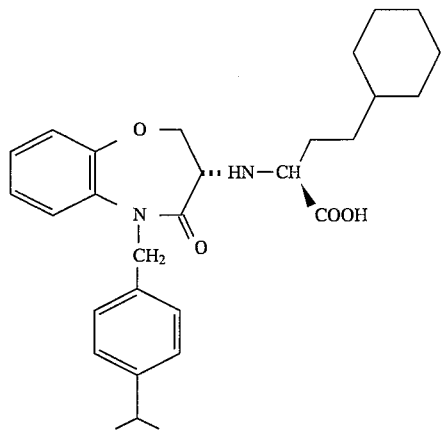

The starting material may be prepared, for example, as follows:

a) (S)-3-(tert-Butoxycarbonylamino)-5-(p-isopropylbenzyl)-2,3,4,5-tetrahydro-1,5-benzoxazepin-4-one 44 g of (S)-3-(tert-butoxycarbonylamino)-2,3-dihydro-1,5(5H)-benzoxazepin-4-one (Chem. Pharm. Bull. 34, 1128 (1986)) are dissolved in 450 ml of absolute dimethylformamide, 44 g of potassium carbonate are added and the batch is stirred at room temperature for 2.5 hours. The first third (of a total of 32 g) of p-isopropylbenzyl chloride and 1.4 g of potassium iodide are added thereto and the batch is stirred at room temperature for 15 hours. The second third of p-isopropylbenzyl chloride is added and, after a further 24 hours, the last third is added, whereupon the batch is stirred again for 48 hours. The reaction mixture is concentrated under a high vacuum, taken up in ethyl acetate, washed with water, with dilute hydrochloric acid and again with water, and dried over sodium sulfate. Flash chromatography (900 g of silica gel, eluant petroleum ether/ethyl acetate 4:1) yields the product in the form of a resin. $R_f$ value (eluant hexane/ethyl acetate 1:4): 0.33.

b) (S)-3-Amino-5-(p-isopropylbenzyl)-4-oxo-2,3,4,5-tetrahydro-1,5-benzoxazepine hydrochloride 55 g of (S)-3-(tert-butoxycarbonylamino)-5-(p-isopropylbenzyl)-2,3,4,5-tetrahydro-1,5-benzoxazepin-4-one are dissolved in 180 ml of approximately 5 hydrochloric acid in ethyl acetate, foaming occurring. After stirring for two hours, the ochre-coloured suspension is concentrated and recrystallised from ether. The hygroscopic product has a m.p. of 215° C. (decomp.).

c) 3-(S)-[(1-(S)Ethoxycarbonyl-3-cyclohexylpropyl)amino]-5-(p-isopropylbenzyl)-4-oxo-2,3,4,5-tetrahydro-1, 5-benzoxazepine 1.5 g of (S)-3-amino-4-oxo-5-(p-isopropylbenzyl)-2,3,4, 5-tetrahydro- 1,5-benzoxazepine hydrochloride, 2.93 g of (R)-alpha-[[(4-nitrophenyl)sulfonyl]oxy]-4-cyclohexylbutyric acid ethyl ester (Helv. Chim. Acta 71 (2), 337, 1988), 1.85 ml of N-methylmorpholine and 2 ml of dimethylformamide are heated at 75° C. for 3 days. The reaction mixture is concentrated and separated by means of flash chromatography (230 g of silica gel, eluant hexane/ethyl acetate 4:1). The product is obtained in the form of a colourless resin. $R_f$ value (eluant hexane/ethyl acetate 4:1): 0.36.

EXAMPLE 2

3-(R)-[(1-(S)-Carboxy-3-cyclohexylpropyl)amino]-5-(p-isopropylbenzyl)-4-oxo-2,3,4,5-tetrahydro-1,5-benzoxazepine Obtained analogously to Example 1, starting from 1.3 g of 3-(R)-[(1-(S)-ethoxycarbonyl-3-cyclohexylpropyl)amino]-5-(p-isopropylbenzyl)-4-oxo-2,3,4,5-tetrahydro-1,5-benzoxazepine. Crystallisation from pentane, m.p. about 80° C. (amorphous). $R_f$ value (eluant: methylene chloride/methanol/conc. ammonia 60:10:1): 0.5. Crystallisation from ether.

The starting material may be prepared, for example, as follows:

a) (R)-3-(tert-Butoxycarbonylamino)-5-(p-isopropylbenzyl)-2,3,4,5-tetrahydro-1,5-benzoxazepin-4-one Obtained analogously to the directions in Example 1a) starting from 4.8 g of (R)-3-(tert-butoxycarbonyl-amino)-2,3-dihydro-1,5-benzoxazepin-4-one (prepared analogously to (S)-3-(tert-butoxycarbonylamino)-2,3-dihydro-1,5-benzoxazepin-4-one, starting from N-Boc-(D)-serine), 4.4 g of p-isopropylbenzyl chloride, 2.9 g of potassium carbonate and 166 mg of potassium iodide. $R_f$ value (eluant: hexane/ethyl acetate 4:1): 0.33.

b) (R)-3-Amino-5-(p-isopropylbenzyl)-4-oxo-2,3,4,5-tetrahydro-1,5-benzoxazepine hydrochloride Obtained analogously to the directions in Example 1b) starting from 6.1 g of (R)-3-(tert-butoxycarbonylamino)-2,3,4,5-tetrahydro-5-(p-isopropylbenzyl)-1,5-benzoxazepin-4-one. M.p. 214° C. (decomp.).

c) 3-(R)-[(1-(S)-Ethoxycarbonyl-3-cyclohexylpropyl)amino]-5-(p-isopropylbenzyl)-4-oxo-2,3,4,5-tetrahydro-1,5-benzoxazepine Obtained analogously to the directions in Example 1c) starting from (R)-3-amino-5-(p-isopropylbenzyl)-4-oxo-2,3,4,5-tetrahydro-1,5-benzoxazepine hydrochloride, 2.93 g of (R)-alpha-[[(4-nitrophenyl)sulfonyl]oxy]-4-cyclohexylbutyric acid ethyl ester and 1.85 ml of N-methylmorpholine. Colourless resin, $R_f$ value (eluant hexane/ethyl acetate 4:1): 0.36.

EXAMPLE 3

The following may be prepared in an analogous manner, for example as described in Example 1 or 2:

3-(S)-[(1-(S)-carboxy-ethyl)amino]-5-(p-isopropylbenzyl)-4-oxo-2,3,4,5-tetrahydro-1,5-benzoxazepine; m.p. 200°;

3-(R)-[(1-(S)-carboxy-ethyl)amino]-5-(p-isopropylbenzyl)-4-oxo-2,3,4,5-tetrahydro-1,5-benzoxazepine;

3-(S)-[(1-(S)-carboxy-propyl)amino]-5-(p-isopropylbenzyl)-4-oxo-2,3,4,5-tetrahydro-1,5-benzoxazepine; m.p. of the hydrochloride: 120°;

3-(R)-([1-(S)-carboxy-propyl)amino]-5-(p-isopropylbenzyl)-4-oxo-2,3,4,5-tetrahydro-1,5-benzoxazepine;

3-(S)-[(1-(S)-carboxy-isobutyl)amino]-5-(p-isopropylbenzyl)-4-oxo-2,3,4,5-tetrahydro-1,5-benzoxazepine; m.p. of the hydrochloride: 160° (decomp.);

3-(R)-[(1-(S)-carboxy-isobutyl)amino]-5-(p-isopropylbenzyl)-4-oxo-2,3,4,5-tetrahydro-1,5-benzoxazepine;

3-(S)-[(1-(S)-carboxy-butyl)amino]-5-(p-isopropylbenzyl)-4-oxo-2,3,4,5-tetrahydro-1,5-benzoxazepine; m.p. of the hydrochloride: 100°;

3-(R)-[(1-(S)-carboxy-butyl)amino]-5-(p-isopropylbenzyl)-4-oxo-2,3,4,5-tetrahydro-1,5-benzoxazepine;

3-(S)-[(1-(S)-carboxy-pentyl)amino]-5-(p-isopropylbenzyl)-4-oxo-2,3,4,5-tetrahydro-1,5-benzoxazepine; m.p. of the hydrochloride: 145° (decomp.);

3-(S)-[(1-(R)-carboxy-pentyl)amino]-5-(p-isopropylbenzyl)-4-oxo-2,3,4,5-tetrahydro-1,5-benzoxazepine; m.p. of the hydrochloride: 130° (decomp.);

3-(S)-[(1-(S)-carboxy-isopentyl)amino]-5-(p-isopropylbenzyl)-4-oxo-2,3,4,5-tetrahydro-1,5-benzoxazepine; m.p. of the hydrochloride: 155° (decomp.);

3-(R)-[(1-(S)-carboxy-isopentyl)amino]-5-(p-isopropylbenzyl)-4-oxo-2,3,4,5-tetrahydro-1,5-benzoxazepine;

3-(S)-[(1-(S)-carboxy-2-cyclohexyl-ethyl)amino]-5-(p-isopropylbenzyl)-4-oxo-2,3,4,5-tetrahydro-1,5-benzoxazepine; m.p. of the hydrochloride: 166° (decomp.);

3-(S)-[(1-(R)-carboxy-2-cyclohexyl-ethyl)amino]-5-(p-isopropylbenzyl)-4-oxo-2,3,4,5-tetrahydro-1,5-benzoxazepine;

3-(S)-[(1-(S)-carboxy-2-phenyl-ethyl)amino]-5-(p-isopropylbenzyl)-4-oxo-2,3,4,5-tetrahydro-1,5-benzoxazepine; m.p. of the hydrochloride: 100°;

3-(R)-[(1-(S)-carboxy-2-phenyl-ethyl)amino]-5-(p-isopropylbenzyl)-4-oxo-2,3,4,5-tetrahydro-1,5-benzoxazepine;

3-(S)-[1-(S)-carboxy-2-(p-methoxyphenyl)-ethyl]amino-5-(p-isopropylbenzyl)-4-oxo-2,3,4,5-tetrahydro-1,5-benzoxazepine; m.p. of the hydrochloride: 110°;

3-(S)-[1-(R)-carboxy-2-(p-methoxyphenyl)-ethyl]amino-5-(p-isopropylbenzyl)-4-oxo-2,3,4,5-tetrahydro-1,5-benzoxazepine; m.p. of the hydrochloride: 120°;

3-(S)-[1-(S)-carboxy-2-(p-fluorophenyl)-ethyl]amino-5-(p-isopropylbenzyl)-4-oxo-2,3,4,5-tetrahydro-1,5-benzoxazepine; m.p. of the hydrochloride: 90°;

3-(R)-[1-(S)-carboxy-2-(p-fluorophenyl)-ethyl]amino-5-(p-isopropylbenzyl)-4-oxo-2,3,4,5-tetrahydro-1,5-benzoxazepine;

3-(S)-[(1-(S)-carboxy-3-phenyl-propyl)amino]-5-(p-isopropylbenzyl)-4-oxo-2,3,4,5-tetrahydro-1,5-benzoxazepine; m.p. of the hydrochloride: 191°–195°;

3-(R)-[(1-(S)-carboxy-3-phenyl-propyl)amino]-5-(p-isopropylbenzyl)-4-oxo-2,3,4,5-tetrahydro-1,5-benzoxazepine.

EXAMPLE 4

In an analogous manner, for example as described in Example 1, 3-(S)-[(1-(S)-carboxy-ethyl)amino]-5-(p-isopropylbenzyl)-4-oxo-2,3,4,5-tetrahydro-1,5-benzoxazepine may be prepared starting from 400 mg of 3-(S)-[(1-(S)-ethoxycarbonyl-ethyl)amino]-5-(p-isopropylbenzyl)-4-oxo-2,3,4,5-tetrahydro-1,5-benzoxazepine by means of hydrolysis with dilute aqueous NaOH solution, m.p. 200° C.

The starting material may be prepared, for example, as follows:

3-(S)-[(1-(S)-ethoxycarbonyl-ethyl)amino]-5-(p-isopropylbenzyl)-4-oxo-2,3,4,5-tetrahydro-1,5-benzoxazepine.

Obtained analogously to Example 1c) starting from 600 mg of (R)-3-amino-4-oxo-2,3,4,5-tetrahydro-5-(p-isopropylbenzyl)-1,5(5H)-benzoxazepine hydrochloride, 1.57 g of (R)-alpha-[[(4-nitrophenyl)sulfonyl]oxy]-propionic acid ethyl ester and 0.76 ml of N-methylmorpholine. $R_f$ value (eluant hexane/ethyl acetate 2:1) 0.27.

(R)-alpha-[[(4-nitrophenyl)sulfonyl]oxy]-propionic acid ethyl ester was obtained analogously to the sulfonic acid ester described in Example 1c), starting from 10.3 g of D-lactic acid ethyl ester, 21.3 g of 4-nitrobenzenesulfonyl chloride and 14.6 ml of triethylamine. $R_f$ value (eluant hexane/ethyl acetate 2:1) 0.44.

EXAMPLE 5

In an analogous manner, for example as described in Example 1, 3-(S)-[(1-(S)-carboxy-3-methylbutyl)amino]-5-(p-isopropylbenzyl)-4-oxo-2,3,4,5-tetrahydro-1,5-benzoxazepine hydrochloride may be prepared starting from 650 mg of 3-(S)-[(1-(S)-benzyloxycarbonyl-3-methylbutyl)amino]-5-(p-isopropylbenzyl)-4-oxo-2,3,4,5-tetrahydro-1,5-benzoxazepine by hydrogenation under normal pressure at room temperature in the presence of 300 mg of palladium-on-carbon in 20 ml of dioxane (10%). After removal of the catalyst by filtration, the product is converted into the hydrochloride by treatment with 3.7N HCl in ethyl acetate. M.p. 155° C. (decomp.).

The starting material may be prepared, for example, as follows:

15 g of D-leucine are placed in 172 ml of 1N aqueous sulfuric acid with cooling with an ice bath and, over a period of 1 hour, 11.8 g of sodium nitrite in 45 ml of water are added thereto. The reaction solution is stirred overnight at room temperature, adjusted to pH=6 with sodium hydrogen carbonate, concentrated to approximately 60 ml, and adjusted to pH=3 with 40% phosphoric acid. The batch is extracted three times with tetrahydrofuran, and the organic phase is washed with brine, dried and concentrated. The crude product is repeatedly concentrated by evaporation with toluene. Hexane is added to the residue, as a result of which the product (R)-alpha-[[(4-nitrophenyl)sulfonyl]oxy]-4-methylvaleric acid precipitates in the form of white crystals (m.p. 60°–62° C., after drying).

13.5 g of (R)-alpha-[[(4-nitrophenyl)sulfonyl]oxy]-4-methylvaleric acid are heated at reflux for 6 hours with 42.1 ml of benzyl alcohol and 2.3 ml of thionyl chloride using a water separator. After cooling, the dark yellow solution is concentrated by evaporation, taken up in ethyl acetate, washed with brine, dried and concentrated. Distillation at 118°–120° C./0.16 mbar yields the pure benzyl ester.

(R)-alpha-[[(4-nitrophenyl)sulfonyl]oxy]-2-(4-methylvaleric acid benzyl ester are obtained analogously to the sulfonic acid ester described in Example 1c) starting from 12.5 g of 2-(R)-hydroxy-5-valeric acid benzyl ester, 13.7 g of 4-nitrobenzenesulfonyl chloride and 9.4 ml of triethylamine. $R_f$ value (eluant hexane/ethyl acetate 2:1) 0.44. $R_f$ value (eluant hexane/ethyl acetate 2:1) 0.46.

3-(S)-[(1-(S)-benzyloxycarbonyl-1-isobutyl)amino]-5-(p-isopropylbenzyl)-4-oxo-2,3,4,5-tetrahydro-1,5-benzoxazepine was obtained analogously to Example 1c) starting from 600 mg of (S)-3-amino-4-oxo-2,3,4,5-tetrahydro-5-(p-isopropylbenzyl)-1,5(5H)-benzoxazepine hydrochloride, 2.1 g of (R)-alpha-[[(4-nitrophenyl)sulfonyl]oxy]-4-methylvaleric acid benzyl ester and 0.76 ml of N-methylmorpholine. $R_f$ value (eluant hexane/ethyl acetate 2:1) 0.56.

EXAMPLE 6

In an analogous manner, for example as described in Example 1, 3-(S)-[(1-(S)-carboxy-2-methylpropyl)amino]-5-(p-isopropylbenzyl)-4-oxo-2,3,4,5-tetrahydro-1,5-benzoxazepine hydrochloride may be prepared starting from 600 mg of 3-(S)-[(1-(S)-benzyloxycarbonyl-1-isopropyl)amino]-5-(p-isopropylbenzyl)-4-oxo-2,3,4,5-tetrahydro-1,5-benzoxazepine by hydrogenation under normal pressure at room temperature in the presence of 200 mg of palladium-on-carbon in 20 ml of dioxane (10%). After removal of the catalyst by filtration, the product is converted into the hydrochloride by treatment with 3.7N HCl in ethyl acetate. M.p. 160° C. (decomp.).

The starting material may be prepared, for example, as follows:

3-(S)-[(1-(S)-Benzyloxycarbonyl-1-isobutyl)amino]-5-(p-isopropylbenzyl)-4-oxo-2,3,4,5-tetrahydro-1,5-benzoxazepine was obtained analogously to Example 1c) starting from 600 mg of (S)-3-amino-4-oxo-2,3,4,5-tetrahydro-5-(p-isopropylbenzyl)-1,5(5H)-benzoxazepine hydrochloride, 1.77 g of (R)-alpha-[[trifluoromethanesulfonyl]oxy]-3-methylbutyric acid benzyl ester (Tetrahedron 19, 6623, 1990) and 0.76 ml of N-methylmorpholine. $R_f$ value (eluant hexane/ethyl acetate 4:1) 0.26.

EXAMPLE 7

In an analogous manner, for example as described in Example 1, 3-(S)-[(1-(S)-carboxy-2-cyclohexylethyl)amino]-5-(p-isopropylbenzyl)-4-oxo-2,3,4,5-tetrahydro-1,5-benzoxazepine hydrochloride may be prepared starting from 520 mg of 3-(S)-[(1-(S)-benzyloxycarbonyl-2-cyclohexylethyl)amino]-5-(p-isopropylbenzyl)-4-oxo-2,3,4,5-tetrahydro-1,5-benzoxazepine by hydrogenation under normal pressure at room temperature with palladium-on-carbon (10%) in 10 ml of dioxane. The product of the hydrogenation is converted into the hydrochloride by treatment with 5N HCl in ethyl acetate and dried. M.p. 166° C. (decomp.).

The starting material may be prepared analogously to Example 5 as follows:

1.5 g of D-phenyllactic acid are hydrogenated under normal pressure for 2 hours in the presence of 0.25 g of "Nishimura" catalyst ($Rh_2O_3/PtO_2$, Degussa) in 20 ml of methanol until saturation is achieved. After removal of the catalyst by filtration followed by concentration, the product is obtained in the form of a yellow oil. $R_f$ value (eluant: toluene/methylene chloride/ethyl acetate/formic acid 16:40:40:4) 0.52.

1.9 g of (R)-alpha-[[(4-nitrophenyl)sulfonyl]oxy]-3-cyclohexylpropionic acid are heated at reflux for 20 hours using a water separator with 2.27 ml of benzyl alcohol and 0.1 ml of thionyl chloride. After cooling, the dark yellow solution is concentrated by evaporation, taken up in ethyl acetate, washed with brine, dried and concentrated Flash chromatography (eluant: petroleum ether/ethyl acetate 17:3) yields the pure product in the form of a colourless resin. $R_f$ value (eluant hexane/ethyl acetate 4:1) 0.27.

(R)-alpha-[[(4-Nitrophenyl)sulfonyl]oxy]-3-cyclohexylpropionic acid benzyl ester was obtained analogously to the sulfonic acid ester described in Example 1c) starting from 1.9 g of 2-(R)-3-cyclohexylpropionic acid benzyl ester, 1.8 g of 4-nitrobenzenesulfonyl chloride and 1.21 ml of triethylamine. $R_f$ value (eluant hexane/ethyl acetate 4:1) 0.41.

837 mg of (S)-3-amino-4-oxo-2,3,4,5-tetrahydro-5-(p-isopropylbenzyl)-1,5(5H)-benzoxazepine hydrochloride, 3.45 g of (R)-alpha-[[(4-nitrophenyl)sulfonyl]oxy]-3-cyclohexylpropionic acid benzyl ester, 1.06 ml of N-methylmorpholine and 4 ml of dimethylformamide are heated at 75° C. for 3 days. The reaction mixture is concentrated and separated by means of flash chromatography (360 g of silica gel, eluant petroleum ether/ethyl acetate 4:1). The product is obtained in the form of a yellowish resin. $R_f$ value (eluant hexane/ethyl acetate 4:1) 0.25.

EXAMPLE 8

In an analogous manner, for example as described in Example 1, 3-(S)-[(1-(S)-carboxy-2-phenylethyl)amino]-5-(p-isopropylbenzyl)-4-oxo-2,3,4,5-tetrahydro-1,5-benzoxazepine hydrochloride may be prepared, obtained analogously to Example 5 by hydrogenation of 0.41 g of 3-(S)-[(1-(S)-benzyloxycarbonyl-2-phenylethyl)amino]-5-(p-isopropylbenzyl)-4-oxo-2,3,4,5-tetrahydro-1,5-benzoxazepine in the presence of 0.2 g of palladium-on-carbon (10%) in 10 ml of dioxane. M.p. 100° C., $R_f$ value (eluant methylene chloride/methanol/conc. ammonia 60:10:1) 0.23.

The starting material may be prepared analogously to Example 5, for example as follows:

Starting from 11 g of D-phenyllactic acid benzyl ester, 10.5 g of 4-nitrobenzenesulfonyl chloride and 6 ml of triethylamine, (R)-alpha-[[(4-nitrophenyl)sulfonyl]oxy]-3-phenylpropionic acid benzyl ester is obtained. $R_f$ value (eluant ethyl acetate/hexane 1:4) 0.3.

Starting from 2.55 g of (R)-alpha-[[(4-nitrophenyl)sulfonyl]-oxy]-3-phenylpropionic acid benzyl ester, 800 mg of (R)-3-amino-4-oxo-2,3,4,5-tetrahydro-5-(p-isopropylbenzyl)-1,5(5H)-benzoxazepine hydrochloride and 0.88 ml of N-methylmorpholine, 3-(S)-[(1-(S)-benzyloxycarbonyl-2-phenylethyl)amino]-5-(p-isopropylbenzyl)-4-oxo-2,3,4,5-tetrahydro-1,5-benzoxazepine is obtained in the form of a yellow oil after flash chromatography (1 kg of silica gel, eluant petroleum ether/ethyl acetate 3:1). $R_f$ value (eluant petroleum ether/ethyl acetate 3:1) 0.19.

EXAMPLE 9

In an analogous manner, for example as described in Example 1, 3-(S)-[(1-(S)-carboxy-3-phenylpropyl)amino]-5-(p-methylbenzyl)-4-oxo-2,3,4,5-tetrahydro-1,5-benzoxazepine hydrochloride may be prepared, obtained analogously to Example 1 by the hydrolysis of 3-(S)-[(1-(S)-ethoxycarbonyl-3-phenylpropyl)amino]-5-(p-methylbenzyl)-4-oxo-2,3,4,5-tetrahydro-1,5-benzoxazepine. The preparation of the hydrochloride is carried out by treatment with 5N HCl in ethyl acetate. $R_f$ value (eluant methylene chloride/methanol/conc. ammonia 60:10:1) 0.48.

The preparation of (R)-alpha-[[(4-nitrophenyl)sulfonyl]oxy]-4-phenylbutyric acid ethyl ester is described in Helv. Chim. Acta 71 (2), 337, 1988.

EXAMPLE 10

In an analogous manner, for example as described in Example 1, 3-(S)-[(1-(S)-carboxy-3-phenylpropyl)amino]-5-(p-isopropylbenzyl)-4-oxo-2,3,4,5-tetrahydro-1,5-benzoxazepine may be prepared, obtained analogously to Example 8 by the hydrolysis of 0.97 g of 3-(S)-[(1-(S)-ethoxycarbonyl-3-phenylpropyl)amino]-5-(p-isopropylbenzyl)-4-oxo-2,3,4,5-tetrahydro-1,5-benzoxazepine in 22 ml of ethanol, 10 ml of water and 1.55 g of NaOH. $R_f$ value (eluant methylene chloride/methanol/conc. ammonia 60:10:1) 0.23. m.p. 191°–192° C.

The starting material may be obtained, for example, as follows:

17 g of (S)-3-amino-4-oxo-2,3,4,5-tetrahydro-5-(p-isopropylbenzyl)-1,5(5H)-benzoxazepine hydrochloride, 48.2 g of (R)-alpha-[[(4-nitrophenyl)sulfonyl]oxy]-4-phenylbutyric acid ethyl ester and 19 ml of N-methylmorpholine are heated at 80° C. for 12 hours. After cooling, the batch is taken up in ethyl acetate, extracted with aqueous sodium hydrogen carbonate solution, dried and concentrated by evaporation. $R_f$ value (eluant ethyl acetate/hexane 1:2) 0.34.

EXAMPLE 11

In an analogous manner, for example as described in Example 1, 3-(S)-[(1-(S)-carboxy-3-cyclohexylpropyl)amino]-5-(p-methylbenzyl)-4-oxo-2,3,4,5-tetrahydro-1,5-benzoxazepine hydrochloride may be prepared, analogously to Example 1 by the hydrolysis of 29.2 g of 3-(S)-[(1-(S)-ethoxycarbonyl-3-phenylpropyl)amino]-5-(p-methylbenzyl)-4-oxo-2,3,4,5-tetrahydro-1,5-benzoxazepine in 150 ml of EtOH, 76 ml of 2N NaOH and 25 ml of Wasser. The hydrochloride of the product is obtained by treatment with HCl in methylene chloride. M.p. 124°–127° C.

The starting material may be obtained, for example, as follows:

Analogously to the directions in Example 1a), starting from 20 g of (S)-3-tert-butoxycarbonylamino-2,3-dihydro-1,5(5H)-benzoxazepin-4-one, 15 g of p-methylbenzyl bromide and 9.67 g of potassium tert-butanolate in 120 ml of DMF, (S)-3-tert-butoxycarbonylamino-2,3,4,5-tetrahydro-5-(p-methylbenzyl)-1,5(5H)-benzoxazepin-4-one is obtained. $R_f$ value (eluant ethyl acetate/hexane 1:4) 0.28.

Analogously to the directions in Example 1b), starting from 2 g of (R)-3-tert-butoxycarbonylamino-2,3,4,5-tetrahydro-5-(p-methylbenzyl)-1,5(5H)-benzoxazepin-4-one, there is obtained by treatment with HCl in ethyl acetate (15 ml), (S)-3-amino-4-oxo-2,3,4,5-tetrahydro-5-(p-methylbenzyl)-1,5(5H)-benzoxazepine hydrochloride. After concentration of the reaction mixture by evaporation the residue is triturated with ether, by means of which the product is obtained in the form of a beige powder. $R_f$ value (eluant methylene chloride/MeOH 95:5) 0.3.

3-(S)-[(1-(S)-ethoxycarbonyl-3-cyclohexylpropyl)amino]-5-(p-methylbenzyl)-4-oxo-2,3,4,5-tetrahydro-1,5-benzoxazepine is obtained analogously to the directions in Example 1c), starting from 20 g of (S)-3-amino-4-oxo-2,3,4,5-tetrahydro-5-(p-methylbenzyl)-1,5(5H)-benzoxazepine hydrochloride, 37.6 g of (R)-alpha-[[(4-nitrophenyl)sulfonyl]oxy]-4-cyclohexylbutyric acid ethyl ester and 8.6 ml of N-methylmorpholine. The product is obtained in the form of a beige powder after trituration with petroleum ether/methyl-tert-butyl ether (7:1) at −78° C. $R_f$ value (eluant petroleum ether/ethyl acetate 4:1) 0.19.

EXAMPLE 22

In an analogous manner, for example as described in Example 1, 3-(S)-[(1-(S)-carboxy-propyl)amino]-5-(p-isopropylbenzyl)-4-oxo-2,3,4,5-tetrahydro-1,5-benzoxazepine hydrochloride may be prepared, m.p. 120° C., $R_f$ value (eluant methylene chloride/methanol/conc. ammonia 60:10:1) 0.23, analogously to Example 5 starting from D-2-aminobutyric acid.

EXAMPLE 13

In an analogous manner, for example as described in Example 1, 3-(S)-[(1-(S)-carboxy-butyl)amino]-5-(p-isopropylbenzyl)-4-oxo-2,3,4,5-tetrahydro-1,5-benzoxazepine hydrochloride may be prepared, m.p. 100° C., $R_f$ value (eluant methylene chloride/methanol/conc. ammonia 60:10:1) 0.27; analogously to Example 5 starting from D-norvaline.

EXAMPLE 14

In an analogous manner, for example as described in Example 1, 3-(S)-[(1-(S)-carboxy-pentyl)amino]-5-(p-isopropylbenzyl)-4-oxo-2,3,4,5-tetrahydro-1,5-benzoxazepine hydrochloride and 3-(S)-[(1-(R)-carboxy-pentyl)amino]-5-(p-isopropylbenzyl)-4-oxo-2,3,4,5-tetrahydro-1,5-benzoxazepine hydrochloride may be prepared.

1-(S)-isomer: m.p. 145° C., $R_f$ value (eluant methylene chloride/methanol/conc. ammonia 60:10:1) 0.25. Obtained by hydrolysis of the more polar ethyl ester; 1-(R)-isomer: m.p. 130° C. (decomp.). Obtained by hydrolysis of the less polar ethyl ester; analogously to Example 5 starting from D,L-2-hydroxycaproic acid ethyl ester. The two diastereoisomers are separated by flash chromatography at the 3-(S)-[(1-(S)-ethoxycarbonyl-pentyl)amino]-5-(p-isopropylbenzyl)-4-oxo-2,3,4,5-tetrahydro-1,5-benzoxazepine stage. $R_f$ values (eluant ethyl acetate/petroleum ether 15:85) 0.33 and 0.23.

EXAMPLE 15

In an analogous manner, for example as described in Example 1, 3-(S)-[(1-(S)-carboxy-2-(p-methoxyphenyl)ethyl)amino]-5-(p-isopropylbenzyl)-4-oxo-2,3,4,5-tetrahydro-1,5-benzoxazepine hydrochloride and 3-(S)-[(1-(R)-carboxy-2-(p-methoxyphenyl)ethyl)amino]-5-(p-isopropylbenzyl)-4-oxo-2,3,4,5-benzoxazepine hydrochloride may be prepared.

1-(S)-isomer: m.p. 120° C., $R_f$ value (eluant methylene chloride/methanol/conc. ammonia 60:10:1) 0.22. By hydrolysis Of the less polar methyl ester. 1-(R)-isomer: m.p. 110° C., $R_f$ value (eluant methylene chloride/methanol/conc. ammonia 60:10:1) 0.18. By hydrolysis of the more polar methyl ester; analogously to Example 5 starting from D,L-p-methoxyphenylalanine. The two diastereoisomers are separated by flash chromatography at the 3-(S)-[(1-(R/S)-methoxycarbonyl-2-(p-methoxyphenyl)ethyl)amino]-5-(p-isopropylbenzyl)-4-oxo-2,3,4,5-tetrahydro-1,5-benzoxazepine stage. $R_f$ values (eluant ethyl acetate/petroleum ether 4) 0.3 and 0.28.

EXAMPLE 16

In an analogous manner, for example as described in Example 1, 3-(S)-[(1-(S)-carboxy-2-(p-fluorophenyl)ethyl)amino]-5-(p-isopropylbenzyl)-4-oxo-2,3,4,5-tetrahydro-1,5-benzoxazepine hydrochloride may be prepared, m.p. 90° C., $R_f$ value (eluant methylene chloride/methanol/conc. ammonia 60:10:1) 0.24; analogously to Example 5 starting from D-p-fluorophenylalanine.

EXAMPLE 17

In an analogous manner, for example as described in Example 1, 3-(S)-[(1-(S)-carboxy-2-benzyloxy-ethyl)amino]-5-(p-isopropylbenzyl)-4-oxo-2,3,4,5-tetrahydro-1,5-benzoxazepine may be prepared, m.p. 178°–182° C.; analogously to Example 5 starting from D-benzylserine.

EXAMPLE 18

In an analogous manner, for example as described in Example 1, 3-(S)-[(1-(S)-carboxy-3-phenylpropyl)amino]-5-(p-isopropylbenzyl)-4-oxo-2,3,4,5-tetrahydro-1,5-benzoxazepine may be prepared, m.p. 191°–195° C.

EXAMPLE 19

In an analogous manner, for example as described in Example 1, 3-(S)-[(1-(S)-carboxy-3-phenylpropyl)amino]-5-(m-methylbenzyl)-4-oxo-2,3,4,5-tetrahydro-1,5-benzoxazepine hydrochloride may be prepared, $R_f$ value (eluant methylene chloride/methanol/conc. ammonia 60:10:1) 0.48, analogously to Example 1 starting from m-methylbenzyl chloride.

EXAMPLE 20

The following may be prepared in an analogous manner, for example as described in one of the preceding Examples:

3-(S)-[(1-(S)-carboxy-3-phenylpropyl)amino]-5-(p-aminobenzyl)-4-oxo-2,3,4,5-tetrahydro-1,5-benzoxazepine;

3-(S)-[(1-(S)-carboxy-3-phenylpropyl)amino]-5-(p-dimethyl-aminobenzyl)-4-oxo-2,3,4,5-tetrahydro-1,5-benzoxazepine;

3-(S)-[(1-(S)-carboxy-3-phenylpropyl)amino]-5-(p-tert-butylbenzyl)-4-oxo-2,3,4,5-tetrahydro-1,5-benzoxazepine;

3-(S)-[(1-(S)-carboxy-3-phenylpropyl)amino]-5-(p-methoxybenzyl)-4-oxo-2,3,4,5-tetrahydro-1,5-benzoxazepine;

3-(S)-[(1-(S)-carboxy-3-phenylpropyl)amino]-5-(p-ethylbenzyl)-4-oxo-2,3,4,5-tetrahydro-1,5-benzoxazepine;

3-(S)-[(1-(S)-carboxy-3-phenylpropyl)amino]-5-(p-nitrobenzyl)-4-oxo-2,3,4,5-tetrahydro-1,5-benzoxazepine;

3-(S)-[(1-(S)-carboxy-3-phenylpropyl)amino]-5-(p-fluorobenzyl)-4-oxo-2,3,4,5-tetrahydro-1,5-benzoxazepine;

3-(S)-[(1-(S)-carboxy-3-phenylpropyl)amino]-5-(p-chlorobenzyl)-4-oxo-2,3,4,5-tetrahydro-1,5-benzoxazepine;

3-(S)-[(1-(S)-carboxy-3-phenylpropyl)amino]-5-(p-bromobenzyl)-4-oxo-2,3,4,5-tetrahydro-1,5-benzoxazepine;

3-(S)-[(1-(S)-carboxy-3-phenylpropyl)amino]-5-(p-iodobenzyl)-4-oxo-2,3,4,5-tetrahydro-1,5-benzoxazepine;

3-(S)-[(1-(S)-carboxy-3-cyclohexylpropyl)amino]-5-(p-aminobenzyl)-4-oxo-2,3,4,5-tetrahydro-1,5-benzoxazepine;

3-(S)-[(1-(S)-carboxy-3-cyclohexylpropyl)amino]-5-(p-dimethylaminobenzyl)-4-oxo-2,3,4,5-tetrahydro-1,5-benzoxazepine;

3-(S)-[(1-(S)-carboxy-3-cyclohexylpropyl)amino]-5-(p-tert-butylbenzyl)-4-oxo-2,3,4,5-tetrahydro-1,5-benzoxazepine;

3-(S)-[(1-(S)-carboxy-3-cyclohexylpropyl)amino]-5-(p-methoxybenzyl)-4-oxo-2,3,4,5-tetrahydro-1,5-benzoxazepine;

3-(S)-[(1-(S)-carboxy-3-cyclohexylpropyl)amino]-5-(p-ethylbenzyl)-4-oxo-2,3,4,5-tetrahydro-1,5-benzoxazepine;

3-(S)-[(1-(S)-carboxy-3-cyclohexylpropyl)amino]-5-(p-nitrobenzyl)-4-oxo-2,3,4,5-tetrahydro-1,5-benzoxazepine;

3-(S)-[(1-(S)-carboxy-3-cyclohexylpropyl)amino]-5-(p-fluorobenzyl)-4-oxo-2,3,4,5-tetrahydro-1,5-benzoxazepine;

3-(S)-[(1-(S)-carboxy-3-cyclohexylpropyl)amino]-5-(p-chlorobenzyl)-4-oxo-2,3,4,5-tetrahydro-1,5-benzoxazepine;

3-(S)-[(1-(S)-carboxy-3-cyclohexylpropyl)amino]-5-(p-bromobenzyl)-4-oxo-2,3,4,5-tetrahydro-1,5-benzoxazepine;

3-(S)-[(1-(S)-carboxy-3-cyclohexylpropyl)amino]-5-(p-iodobenzyl)-4-oxo-2,3,4,5-tetrahydro-1,5-benzoxazepine;

3-(S)-[(1-(S)-carboxy-2-cyclohexylethyl)amino]-5-(p-aminobenzyl)-4-oxo-2,3,4,5-tetrahydro-1,5-benzoxazepine;

3-(S)- [(1-(S)-carboxy-2-cyclohexylethyl)amino]-5-(p-dimethylaminobenzyl)-4-oxo-2,3,4,5-tetrahydro-1,5-benzoxazepine;

3-(S)-[(1-(S)-carboxy-2-cyclohexylethyl)amino]-5-(p-tert-butylbenzyl)-4-oxo-2,3,4,5-tetrahydro-1,5-benzoxazepine;

3-(S)-[(1-(S)-carboxy-2-cyclohexylethyl)amino]-5-(p-methoxybenzyl)-4-oxo-2,3,4,5-tetrahydro-1,5-benzoxazepine;

3-(S)-[(1-(S)-carboxy-2-cyclohexylethyl)amino]-5-(p-ethylbenzyl)-4-oxo-2,3,4,5-tetrahydro-1,5-benzoxazepine;

3-(S)-[(1-(S)-carboxy-2-cyclohexylethyl)amino]-5-(p-nitrobenzyl)-4-oxo-2,3,4,5-tetrahydro-1,5-benzoxazepine;

3-(S)-[(1-(S)-carboxy-2-cyclohexylethyl)amino]-5-(p-fluorobenzyl)-4-oxo-2,3,4,5-tetrahydro-1,5-benzoxazepine;

3-(S)-[(1-(S)-carboxy-2-cyclohexylethyl)amino]-5-(p-chlorobenzyl)-4-oxo-2,3,4,5-tetrahydro-1,5-benzoxazepine;

3-(S)-[(1-(S)-carboxy-2-cyclohexylethyl)amino]-5-(p-bromobenzyl)-4-oxo-2,3,4,5-tetrahydro-1,5-benzoxazepine;

3-(S)-[(1-(S)-carboxy-2-cyclohexylethyl)amino]-5-(p-iodobenzyl)-4-oxo-2,3,4,5-tetrahydro-1,5-benzoxazepine;

3-(S)-[(1-(S)-carboxy-2-phenylethyl)amino]-5-(p-aminobenzyl)-4-oxo-2,3,4,5-tetrahydro-1,5-benzoxazepine;

3-(S)-[(1-(S)-carboxy-2-phenylethyl)amino]-5-(p-dimethylaminobenzyl)-4-oxo-2,3,4,5-tetrahydro-1,5-benzoxazepine;

3-(S)-[(1-(S)-carboxy-2-phenylethyl)amino]-5-(p-tert-butylbenzyl )-4-oxo-2,3,4,5-tetrahydro-1,5-benzoxazepine;

3-(S)-[(1-(S)-carboxy-2-phenylethyl)amino]-5-(p-methoxybenzyl)- 4-oxo-2,3,4,5-tetrahydro-1,5-benzoxazepine;

3-(S)-[(1-(S)-carboxy-2-phenylethyl)amino]-5-(p-ethylbenzyl)-4-oxo-2 ,3,4,5-tetrahydro-1,5-benzoxazepine;

3-(S)-[(1-(S)-carboxy-2-phenylethyl)amino]-5-(p-nitrobenzyl)-4-oxo-2 ,3,4,5-tetrahydro-1,5-benzoxazepine;

3-(S)-[(1-(S)-carboxy-2-phenylethyl)amino]-5-(p-fluorobenzyl)-4-oxo-2,3,4,5-tetrahydro-1,5-benzoxazepine;

3-(S)-[(1-(S)-carboxy-2-phenylethyl)amino]-5-(p-chlorobenzyl)-4-oxo-2,3,4,5-tetrahydro-1,5-benzoxazepine;

3-(S)-[(1-(S)-carboxy-2-phenylethyl)amino]-5-(p-bromobenzyl)-4-oxo-2,3,4, 5-tetrahydro-1,5-benzoxazepine;

3-(S)-[(1-(S)-carboxy-2-phenylethyl)amino]-5-(p-iodobenzyl)-4-oxo-2,3,4, 5-tetrahydro-1,5-benzoxazepine;

3-(S)-[(1-(S)-carbamoyl-3-cyclohexylpropyl)amino]-5-(p-isopropylbenzyl)-4-oxo-2,3,4,5-tetrahydro-1,5-benzoxazepine;

3-(S)-[(1-(S)-carbamoyl-3-phenylpropyl)amino]-5-(p-isopropylbenzyl)-4-oxo-2,3,4,5-tetrahydro-1,5-benzoxazepine;

3-(S)-[(1-(S)-carbamoyl-2-phenylethyl)amino]-5-(p-isopropylbenzyl)-4-oxo-2,3,4,5-tetrahydro-1,5-benzoxazepine;

3-(S)-[(1-(S)-carbamoyl-2-cyclohexylethyl)amino]-5-(p-isopropylbenzyl)-4-oxo-2,3,4,5-tetrahydro-1,5-benzoxazepine;

3-(S)-[(1-(S)-carbamoyl-3-cyclohexylpropyl)amino]-5-(p-methylbenzyl)-4-oxo-2,3,4,5-tetrahydro-1,5-benzoxazepine;

3-(S)-[(1-(S)-carbamoyl-3-phenyl)propylamino]-5-(p-methylbenzyl)-4-oxo-2,3,4,5-tetrahydro-1,5-benzoxazepine;

3-(S)-[(1-(S)-carbamoyl-2-phenylethyl)amino]-5-(p-methylbenzyl)-4-oxo-2,3,4,5-tetrahydro-1,5-benzoxazepine;

3-(S)-[(1-(S)-carbamoyl-2-cyclohexylethyl)amino]-5-(p-methylbenzyl)-4-oxo-2,3,4,5-tetrahydro-1,5-benzoxazepine;

3-(S)-[(1-(S)-N-hydroxy-carbamoyl-3-cyclohexylpropyl)amino]-5-(p-isopropylbenzyl)-4-oxo-2,3,4,5-tetrahydro-1,5-benzoxazepine;

3-(S)-[(1-(S)-N-hydroxy-carbamoyl-3-phenylpropyl)amino]-5-(p-isopropylbenzyl)-4-oxo-2,3,4,5-tetrahydro-1,5-benzoxazepine;

3-(S)-[(1-(S)-N-hydroxy-carbamoyl-2-phenylethyl)amino]-5-(p-isopropylbenzyl)-4-oxo-2,3,4,5-tetrahydro-1,5-benzoxazepine;

3-(S)-[(1-(S)-N-hydroxy-carbamoyl-2-cyclohexylethyl)amino]-5-(p-isopropylbenzyl)- 4-oxo-2,3,4,5-tetrahydro-1,5-benzoxazepine;

3-(S)-[(1-(S)-N-hydroxy-carbamoyl-3-cyclohexylpropyl)amino]-5-(p-methylbenzyl)-4-oxo-2,3,4,5-tetrahydro-1,5-benzoxazepine;

3-(S)-[(1-(S)-N-hydroxy-carbamoyl-3-phenylpropyl)amino]-5-(p-methylbenzyl)-4-oxo-2,3,4,5-tetrahydro-1,5-benzoxazepine;

3-(S)-[(1-(S)-N-hydroxy-carbamoyl-2-phenylethyl)amino]-5-(p-methylbenzyl)-4-oxo-2,3,4,5-tetrahydro-1,5-benzoxazepine;

3-(S)-[(1-(S)-N-hydroxy-carbamoyl-2-cyclohexylethyl)amino]-5-(p-methylbenzyl)-4-oxo-2,3,4,5-tetrahydro-1,5-benzoxazepine;

EXAMPLE 21

Tablets, each comprising 50 mg of active ingredient, e.g. 3-(S)-[(1-(S)-carboxy-3-cyclohexyl-propyl)-amino]-5-(p-isopropylbenzyl)-4-oxo-2,3,4,5-tetrahydro-1,5-benzoxazepine, may be prepared as follows:

| Composition (for 10 000 tablets): | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of potato starch and the mixture is moistened with an alcoholic solution of the gelatin and granulated through a sieve. After drying the granules, the remainder of the potato starch, the talc, the magnesium stearate and the highly dispersed silicon dioxide are added thereto and the mixture is compressed to form tablets, each weighing 145.0 mg and comprising 50.0 mg of active ingredient, which may, if desired, be provided with breaking notches for the purpose of finer adjustment of the dose.

EXAMPLE 22

Film-coated tablets, each comprising 100 mg of active ingredient, e.g. 3-(S)-[(1-(S)-carboxy-3-cyclohexylpropyl)amino]-5-(p-isopropylbenzyl)-4-oxo-2,3,4,5-tetrahydro-1, 5-benzoxazepine, may be prepared as follows:

| Composition (for 1000 tablets): | |
|---|---|
| active ingredient | 100.00 g |
| lactose | 100.00 g |
| corn starch | 70.00 g |
| talc | 8.50 g |
| calcium stearate | 1.50 g |
| hydroxypropylmethylcellulose | 2.36 g |
| shellac | 0.64 g |
| water | q.s. |
| dichloromethane | q.s. |

The active ingredient, the lactose and 40 g of the corn starch are mixed and moistened with a paste prepared from 15 g of corn starch and water (with heating) and granulated. The granules are dried, and the remainder of the corn starch, the talc and the calcium stearate are added and mixed with the granules. The mixture is compressed to form tablets (weight: 280 mg) which are then film-coated with a solution of the hydroxypropylmethylcellulose and the shellac in dichloromethane (final weight of the film-coated tablet: 283 mg).

EXAMPLE 23

In an analogous manner, for example as described in Examples 20 and 21, it is also possible to prepare tablets and film-coated tablets comprising a different compound of formula I or a pharmaceutically acceptable salt of a compound of formula I, e.g. according to any one of Examples 1 to 20.

We claim:

1. A 3-amino-1-arylalkyl-benzazepin-2-one of the general formula

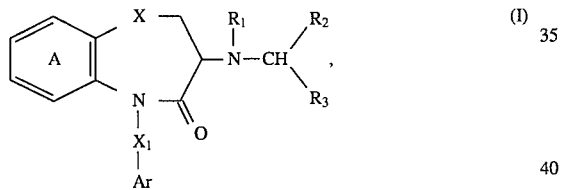

wherein

Ar is selected from the group consisting of phenyl, naphthyl, monocyclic, monoza-, monooxa-, monothia-, diaza-, oxaza- and thiaza-aryl;

X is —O— or —S(O)$_n$ and n is 0, 1 or 2;

$X_1$ is $C_1$-$C_2$ alkylene or a direct bond;

$R_1$ is hydrogen, lower alkyl, pyrrolyl, pyridyl, furyl, thienyl, imidazolyl, isoxazolyl, thiazolyl lower alkanoyl, aroyl, or benzoyl;

$R_2$ is lower alkyl, hydroxy-lower alkyl, lower alkoxy-lower alkyl, pyrrolyl, pyridyl, furyl, thienyl, imidazolyl, isoxazolyl, thiazolyl or $C_3$-$C_7$cycloalkyl-lower alkyl;

$R_3$ is carboxy; lower alkoxycarbonyl; lower alkoxy-lower alkoxycarbonyl; pyrrolyl, pyridyl, furyl, thienyl, imidazolyl, isoxazolyl, thiazolyl; carbamoyl; carbamoyl that (I) is monosubstituted or disubstituted, the substituents being independent of one another, by lower alkyl, lower alkenyl, lower alkynyl or by phenyl-lower alkyl or (iii) is disubstituted by lower alkylene or by lower alkylene-$Z_1$-lower alkylene, $Z_1$ being O, S or NH; 5-tetrazolyl; Po$_2$H$_2$; PO$_3$H$_2$ or SO$_3$H$_2$; the ring A and aromatic radicals are, independently of one another, unsubstituted or mono- or poly-substituted by substituents selected from the group consisting of: lower alkyl, pyrrolyl, pyridyl, furyl, thienyl, imidazolyl, isoxazolyl, thiazolyl, lower alkoxy-lower alkyl, lower alkoxy, lower alkoxy-lower alkoxy, $C_3$-$C_7$ cycloalkyl, $C_3$-$C_7$ cycloalkyl-lower alkyl, nitrol, halogen, trifluoromethyl, amino and amino that is monosubstituted or disubstituted, the substituents being independent of one another, by lower alkyl, pyrrolyl, pyridyl, furyl, thienyl, imidazolyl, isoxazolyl, thiazolyl or by phenyl, naphthyl, monocyclic, monoza-, monooxa-, monothia-, diaza-, oxaza- and thiaza-aryl, or disubstituted by lower alkylene or by lower alkyleneoxy-lower alkylene;

a steroisomer or a salt thereof.

2. A compound according to claim 1 of formula I wherein

Ar is phenyl;

X is —O— or —S(O)$_n$— and n is 0, 1 or 2;

$X_1$ is $C_1$-$C_2$alkylene or a direct bond;

$R_1$ is hydrogen, lower alkyl, lower alkyl that is substituted by phenyl, naphthyl, pyrrolyl, pyridyl, furyl, thienyl, imidazolyl, isoxazolyl or by thiazolyl, lower alkanoyl, lower alkanoyl that is substituted by phenyl, naphthyl, pyrrolyl, pyridyl, furyl, thienyl, imidazolyl, isoxazolyl or by thiazolyl, or benzoyl;

$R_2$ is (i) lower alkyl, lower alkyl that is substituted by phenyl, naphthyl, pyrrolyl, pyridyl, furyl, thienyl, imidazolyl, isoxazolyl or by thiazolyl, or $C_1$-$C_7$cycloalkyl-lower alkyl, or (ii) hydroxy-lower alkyl, lower alkoxy-lower alkyl, or lower alkoxy-lower alkyl in which the lower alkoxy moiety is substituted by phenyl, naphthyl, pyrrolyl, pyridyl, furyl, thienyl, imidazolyl, isoxazolyl or by thiazolyl;

$R_3$ is (i) carboxy, 5-tetrazolyl, PO$_2$H$_2$, PO$_3$H$_2$ or SO$_3$H$_2$ or (ii) lower alkoxycarbonyl, lower alkoxy-lower alkoxycarbonyl, phenyl-lower alkoxycarbonyl, benzoylcarbonyl, carbamoyl, lower alkylcarbamoyl, di-lower alkylcarbamoyl, phenyl-lower alkylcarbamoyl, diphenyl-lower alkylcarbamoyl, hydroxycarbamoyl, lower alkanesulfonyl-carbamoyl, halo-lower alkanesulfonyl or phenylsulfonyl;

the ring A and aromatic radicals are, independently of one another, unsubstituted or mono- or poly-substituted by substituents selected from the group consisting of: lower alkyl, lower alkyl that is substituted by phenyl, naphthyl, pyrrolyl, pyridyl, furyl, thienyl, imidazolyl, isoxazolyl or by thiazolyl, lower alkoxy-lower alkyl, lower alkoxy, lower alkoxy-lower alkoxy, phenyl-lower alkoxy, $C_3$-$C_7$cycloalkyl, $C_3$-$C_7$cycloalkyl-lower alkyl, nitro, halogen, trifluoromethyl, amino and amino that is monosubstituted or disubstituted, the substituents being independent of one another, by lower alkyl, phenyl-lower alkyl or by phenyl or disubstituted by lower alkylene or by lower alkyleneoxy-lower alkylene;

a stereoisomer or a salt thereof.

3. A compound according to claim 1 of formula I wherein

Ar is phenyl;

X is —O— or —S(O)$_n$— and n is 0, 1 or 2;

$X_1$ is $C_1$-$C_2$alkylene or a direct bond;

$R_1$ is hydrogen, lower alkyl, phenyl-lower alkyl, lower alkanoyl, phenyl-lower alkanoyl or benzoyl;

$R_2$ is lower alkyl, phenyl-lower alkyl or $C_3$-$C_7$cycloalkyl-lower alkyl;

$R_3$ is (i) carboxy, 5-tetrazolyl, PO$_2$H$_2$, PO$_3$H$_2$ or SO$_3$H$_2$ or (ii) carbamoyl or hydroxy-carbamoyl;

the ring A and aromatic radicals are, independently of one another, unsubstituted or mono- or poly-substituted by substituents selected from the group consisting of: lower alkyl, phenyl-lower alkyl, lower alkoxy-lower alkyl, lower alkoxy, lower alkoxy-lower alkoxy, phenyl-lower alkoxy, $C_3$-$C_7$cycloalkyl, $C_3$-$C_7$cycloalkyl-lower alkyl, nitro, halogen, trifluoromethyl, amino and amino that is monosubstituted or disubstituted, the substituents being independent of one another, by lower alkyl, phenyl-lower alkyl or by phenyl, or disubstituted by lower alkylene or by lower alkyleneoxy-lower alkylene;

a stereoisomer or a salt thereof.

4. A compound according to claim 1 of formula I wherein

Ar is phenyl or phenyl substituted by $C_1$-$C_4$alkyl;

X is —O— or —S(O)$_n$— and n is 0, 1 or 2;

$X_1$ is $C_1$-$C_2$alkylene or a direct bond;

$R_1$ is hydrogen, $C_1$-$C_4$alkyl or $C_2$-$C_5$alkanoyl;

$R_2$ is phenyl-$C_1$-$C_4$alkyl wherein phenyl is unsubstituted or is substituted by halogen, trifluoromethyl, $C_1$-$C_4$alkyl or by $C_1$-$C_4$alkoxy, or $R_2$ is $C_3$-$C_7$cycloalkyl-$C_1$-$C_4$alkyl;

$R_3$ is carboxy, 5-tetrazolyl, $PO_2H_2$, $PO_3H_2$ or $SO_3H_2$;

the ring A is unsubstituted or mono- or poly-substituted by substituents selected from the group consisting of:
$C_1$-$C_4$alkyl, halogen, $C_3$-$C_7$alkoxy-$C_1$-$C_4$alkyl, $C_1$-$C_4$alkoxy, $C_1$-$C_4$alkoxy-$C_1$-$C_4$alkoxy, nitro, halogen and trifluoromethyl;

a stereoisomer or a salt thereof.

5. A compound according to claim 1 of formula I wherein

Ar is phenyl substituted by $C_1$-$C_4$alkyl, lower alkoxy, halogen, trifluoromethyl, amino, lower alkylamino, di-lower alkylamino or by nitro;

X is —O—;

$X_1$ is methylene;

$R_1$ is hydrogen or $C_2$-$C_5$alkanoyl;

$R_2$ is phenyl-$C_1$-$C_4$alkyl wherein phenyl is unsubstituted or is substituted by halogen, trifluoromethyl, $C_1$-$C_4$alkyl or by $C_1$-$C_4$alkoxy; or $R_2$ is $C_3$-$C_7$cycloalkyl-$C_1$-$C_4$alkyl;

$R_3$ is carboxy, carbamoyl or hydroxycarbamoyl;

the ring A is unsubstituted or mono- or poly-substituted by substituents selected from the group consisting of:
$C_1$-$C_4$alkyl, halogen, $C_1$-$C_4$alkoxy-$C_1$-$C_4$alkyl, $C_1$-$C_4$alkoxy, $C_1$-$C_4$alkoxy-$C_1$-$C_4$alkoxy, nitro, halogen and trifluoromethyl;

a stereoisomer or a salt thereof.

6. A compound according to claim 1 of formula I wherein

Ar is phenyl or phenyl substituted by $C_1$-$C_4$alkyl;

X is —O—;

$X_1$ is methylene;

$R_1$ is hydrogen or $C_2$-$C_5$alkanoyl;

$R_2$ is phenyl-$C_1$-$C_4$alkyl wherein phenyl is unsubstituted or is substituted by halogen, trifluoromethyl, $C_1$-$C_4$alkyl or by $C_1$-$C_4$alkoxy; or $R_2$ is $C_3$-$C_7$cycloalkyl-$C_1$-$C_4$alkyl;

$R_3$ is carboxy or 5-tetrazolyl;

the ring A is unsubstituted or is mono- or poly-substituted by substituents selected from the group consisting of:
$C_1$-$C_4$alkyl, halogen, $C_1$-$C_4$alkoxy-$C_1$-$C_4$alkyl, $C_1$-$C_4$alkoxy, $C_1$-$C_4$alkoxy-$C_1$-$C_4$alkoxy, nitro, halogen and trifluoromethyl;

a stereoisomer or a salt thereof.

7. A compound according to claim 1 of formula

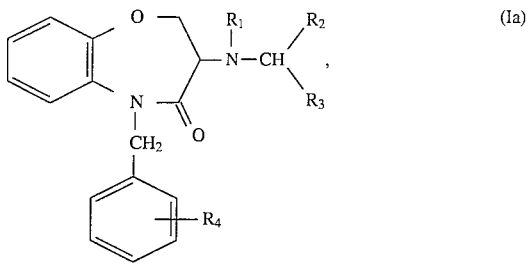

(Ia)

wherein $R_1$ is hydrogen; $R_2$ is phenyl-$C_1$-$C_4$alkyl wherein phenyl is unsubstituted or is substituted by halogen, trifluoromethyl, $C_1$-$C_4$alkyl or by $C_1$-$C_4$alkoxy, or $R_2$ is $C_5$-$C_6$cycloalkyl-$C_1$-$C_4$alkyl; $R_3$ is carboxy; and $R_4$ is $C_1$-$C_4$alkyl; a stereoisomer or a salt thereof.

8. A compound according to claim 1 of formula

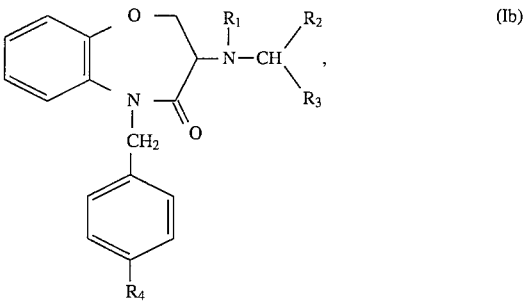

(Ib)

wherein $R_1$ is hydrogen; $R_2$ is phenyl-$C_1$-$C_4$alkyl or $C_5$-$C_6$cycloalkyl-$C_1$-$C_4$alkyl; $R_3$ is carboxy; and $R_4$ is $C_1$-$C_4$alkyl; a stereoisomer or a salt thereof.

9. A compound according to claim 1 of formulae I wherein both the carbon atom having the variables $R_2$ and $R_3$, and the carbon atom to which the amino group is bonded, have the (S)-configuration.

10. A compound selected from 3-(S)-[(1-(S)-carboxy-3-cyclohexylpropyl)amino]-5-(p-isopropylbenzyl)-4-oxo-2,3,4,5-tetrahydro-1,5-benzoxazepine;

3-(R)-[(1-(S)-carboxy-3-cyclohexylpropyl)amino]-5-(p-isopropylbenzyl)-4-oxo-2,3,4,5-tetrahydro-1,5-benzoxazepine;

-3(S)-[(1-(S)-carboxy-ethyl)amino]-5-(p-isopropylbenzyl)-4-oxo-2,3,4,5-tetrahydro-1,5-benzoxazepine;

3-(R)-[(1-(S)-carboxy-ethyl)amino]-5-(p-isopropylbenzyl)-4-oxo-2,3,4,5-tetrahydro-1,5-benzoxazepine;

3-(S)-[(1-(S)-carboxy-propyl)amino]-5-(p-isopropylbenzyl)-4-oxo-2,3,4,5-tetrahydro-1,5-benzoxazepine;

3-(R)-([1-(S)-carboxy-propyl)amino]-5-(p-isopropylbenzyl)-4-oxo-2,3,4,5-tetrahydro-1,5-benzoxazepine;

3-(S)-[(1-(S)-carboxy-isobutyl)amino]-5-(p-isopropyl-benzyl)-4-oxo-2,3,4,5-tetrahydro-1,5-benzoxazepine;

3-(R)-[(1-(S)-carboxy-isobutyl)amino]-5-(p-isopropyl-benzyl)-4-oxo-2,3,4,5-tetrahydro-1,5-benzoxazepine;

3-(S)-[(1-(S)-carboxy-butyl)amino]-5-(p-isopropylbenzyl)-4-oxo-2,3,4,5-tetrahydro-1,5-benzoxazepine;

3-(R)-[(1-(S)-carboxy-butyl)amino]-5-(p-isopropylbenzyl)-4-oxo-2,3,4,5-tetrahydro-1,5-benzoxazepine;

3-(S)-[(1-(S)-carboxy-pentyl)amino]-5-(p-isopropylbenzyl)-4-oxo-2,3,4,5-tetrahydro-1,5-benzoxazepine;

3-(S)-[(1-(R)-carboxy-pentyl)amino]-5-(p-isopropylbenzyl)-4-oxo-2,3,4,5-tetrahydro-1,5-benzoxazepine;

3-(S)-[(1-(S)-carboxy-isopentyl)amino]-5-(p-isopropyl-benzyl)-4-oxo-2,3,4,5-tetrahydro-1,5-benzoxazepine;

3-(R)-[(1-(S)-carboxy-isopentyl)amino]-5-(p-isopropyl-benzyl)-4-oxo-2,3,4,5-tetrahydro-1,5-benzoxazepine;

3-(S)-[(1-(S)-carboxy-2-cyclohexyl-ethyl)amino]-5-(p-isopropylbenzyl)-4-oxo-2,3,4,5-tetrahydro-1,5-benzoxazepine;

3-(S)-[(1-(R)-carboxy-2-cyclohexyl-ethyl)amino]-5-(p-isopropylbenzyl)-4-oxo-2,3,4,5-tetrahydro-1,5-benzoxazepine;

3-(S)-[(1-(S)-carboxy-2-phenyl-ethyl)amino]-5-(p-isopropylbenzyl)-4-oxo-2,3,4,5-tetrahydro-1,5-benzoxazepine;

3-(R)-[(1-(S)-carboxy-2-phenyl-ethyl)amino]-5-(p-isopropylbenzyl)-4-oxo-2,3,4,5-tetrahydro-1,5-benzoxazepine;

3-(S)-[1-(S)-carboxy-2-(p-methoxyphenyl)-ethyl]amino-5-(p-isopropylbenzyl)-4-oxo-2,3,4,5-tetrahydro-1,5-benzoxazepine;

3-(S)-[1-(R)-carboxy-2-(p-methoxyphenyl)-ethyl]amino-5-(p-isopropylbenzyl)- 4-oxo-2,3,4,5-tetrahydro-1,5-benzoxazepine;

3-(S)-[1-(S)-carboxy-2-(p-fluorophenyl)-ethyl]amino-5-(p-isopropylbenzyl)-4-oxo-2,3,4,5-tetrahydro-1,5-benzoxazepine;

3-(R)-[1-(S)-carboxy-2-(p-fluorophenyl)-ethyl]amino-5-(p-isopropylbenzyl)-4-oxo-2,3,4,5-tetrahydro-1,5-benzoxazepine;

3-(S)-[(1-(S)-carboxy-3-phenyl-propyl)amino]-5-(p-isopropylbenzyl)-4-oxo-2,3,4,5-tetrahydro-1,5-benzoxazepine;

3-(R)-[(1-(S)-carboxy-3-phenyl-propyl)amino]-5-(p-isopropylbenzyl)-4-oxo-2,3,4,5-tetrahydro-1,5-benzoxazepine;

or a salt thereof.

11. A compound selected from 3-(S)-[(1-(S)-carboxy-ethyl)amino]-5-(p-isopropylbenzyl)-4-oxo-2,3,4,5-tetrahydro-1,5-benzoxazepine;

3-(S)-[(1-(S)-carboxy-3-methylbutyl)amino]-5-(p-isopropylbenzyl)-4-oxo-2,3,4,5-tetrahydro-1,5-benzoxazepine;

3-(S)-[(1-(S)-carboxy-2-methylpropyl)amino]-5-(p-isopropylbenzyl)-4-oxo-2,3,4,5-tetrahydro-1,5-benzoxazepine;

3-(S)-[(1-(S)-carboxy-2-cyclohexylethyl)amino]-5-(p-isopropylbenzyl)-4-oxo-2,3,4,5-tetrahydro-1,5-benzoxazepine;

3-(S)-[(1-(S)-carboxy-2-phenylethyl)amino]-5-(p-isopropylbenzyl)-4-oxo-2,3,4,5-tetrahydro-1,5-benzoxazepine;

3-(S)-[(1-(S)-carboxy-3-phenylpropyl)amino]-5-(p-methylbenzyl)-4-oxo-2,3,4,5-tetrahydro-1,5-benzoxazepine;

3-(S)-[(1-(S)-carboxy-3-phenylpropyl)amino]-5-(p-isopropylbenzyl)-4-oxo-2,3,4,5-tetrahydro-1,5-benzoxazepine;

3-(S)-[(1-(S)-carboxy-3-cyclohexylpropyl)amino]-5-(p-methylbenzyl)-4-oxo-2,3,4,5-tetrahydro-1,5-benzoxazepine;

3-(S)-[(1-(S)-carboxy-propyl)amino]-5-(p-isopropylbenzyl)-4-oxo-2,3,4,5-tetrahydro-1,5-benzoxazepine;

3-(S)-[(1-(S)-carboxy-butyl)amino]-5-(p-isopropylbenzyl)-4-oxo-2,3,4,5-tetrahydro-1,5-benzoxazepine;

3-(S)-[(1-(S)-carboxy-pentyl)amino]-5-(p-isopropylbenzyl)-4-oxo-2,3,4,5-tetrahydro-1,5-benzoxazepine;

3-(S)-[(1-(R)-carboxy-pentyl)amino]-5-(p-isopropylbenzyl)-4-oxo-2,3,4,5-tetrahydro-1,5-benzoxazepine;

3-(S)-[(1-(S)-carboxy-2-(p-methoxyphenyl)ethyl)amino]-5-(p-isopropylbenzyl)- 4-oxo-2,3,4,5-tetrahydro-1,5-benzoxazepine;

3-(S)-[(1-(R)-carboxy-2-(p-methoxyphenyl)ethyl)amino]-5-(p-isopropylbenzyl)-4-oxo-2,3,4,5-tetrahydro-1,5-benzoxazepine;

3-(S)-[(1-(S)-carboxy-2-(p-fluorophenyl)ethyl)amino]-5-(p-isopropylbenzyl)-4-oxo-2,3,4,5-tetrahydro-1,5-benzoxazepine;

3-(S)-[(1-(S)-carboxy-2-benzyloxy-ethyl)amino]-5-(p-isopropylbenzyl)-4-oxo-2,3,4,5-tetrahydro-1,5-benzoxazepine;

3-(S)-[(1-(S)-carboxy-3-phenylpropyl)amino]-5-(p-isopropylbenzyl)-4-oxo-2,3,4,5-tetrahydro-1,5-benzoxazepine; and 3-(S)-[(1-(S)-carboxy-3-phenylpropyl)amino]-5-(m-methylylbenzyl)-4-oxo-2,3,4,5-tetrahydro-1,5-benzoxazepine;

or a salt thereof in each case.

12. A process for the preparation of a compound of formula I, a stereoisomer or a salt thereof, which comprises a) in a compound of formula

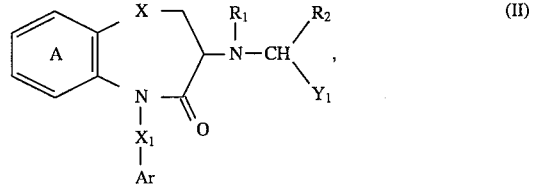

wherein $Y_1$ is a radical that can be converted into the variable $R_3$, or in a salt thereof, converting $Y_1$ into the variable $R_3$; or, b) for the preparation of a compound of formula (I) wherein $R_1$ is hydrogen, or for the preparation of a salt thereof, a compound of formula

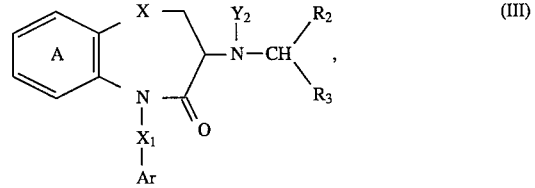

wherein $Y_2$ is an amino-protecting group, or in a salt thereof, removing the amino-protecting group; or c) reacting a compound of formula

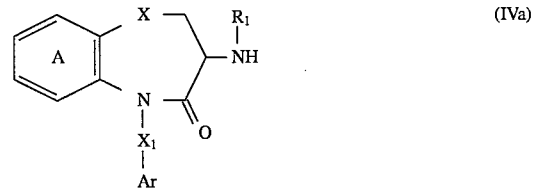

with a compound of formula

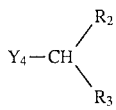

(IVb), wherein $Y_4$ is a nucleofugal leaving group, or with a compound of formula $R_2$—CO—$R_3$ (IVc) or a salt thereof; or d) reacting a compound of formula

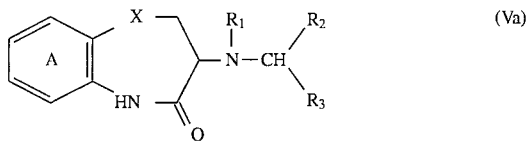

with a compound of formula $Y_6$—$X_1$—Ar (Vb), wherein $Y_6$ is a nucleofugal leaving group, or with a salt thereof; or e) reacting a compound of formula

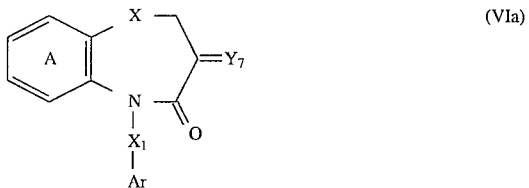

wherein $Y_7$ is (i) oxo or (ii) reactive esterified hydroxy together with hydrogen, with a compound of formula

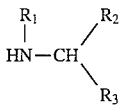

(VIb) or with a salt thereof;

and in each case, if desired, isolating in free form or in salt form a compound of formula I obtainable according to the process or in some other manner, converting a compound of formula I obtainable according to the process or in some other manner into a different compound of formula I, separating a mixture of isomers obtainable according to the process and isolating the desired isomer and/or converting a free compound of formula I obtainable according to the process into a salt or a salt of a compound of formula I obtainable according to the process into the free compound of formula I or into a different salt.

13. A pharmaceutical composition for treating pathological symptoms of the human body that are brought about by modulation of the $AT_2$-receptor comprising as active ingredient a compound according to claim 1, a stereoisomer or a pharmaceutically acceptable salt thereof, where appropriate together with customary excipients.

14. A method of treating pathological symptoms of the human body that are brought about by modulation of the $AT_2$-receptor, which comprises administering a therapeutically effective amount of a compound of formula I according to claim 1, or of a stereoisomer or pharmaceutically acceptable salt thereof.

15. A method of stimulating growth-inhibiting and antiproliferative effects of tyrosine phosphatase comprising administering a therapeutically effective amount of a compound according to claim 1, or of a stereoisomer or a pharmaceutically acceptable salt thereof.

16. A method of treating vascular proliferation disorders comprising administering a therapeutically effective amount of a compound according to claim 1, or of a stereoisomer or a pharmaceutically acceptable salt thereof.

17. A method of treating sterility dysfunction caused by anovulation, ovulation disorders, dysfunction of the corpus luteum and missed abortion comprising administering a therapeutically effective amount of a compound according to claim 1, or of a stereoisomer or a pharmaceutically acceptable salt thereof.

18. A method of treating dysmenorrhoea comprising administering a therapeutically effective amount of a compound according to claim 1, or of a stereoisomer or a pharmaceutically acceptable salt thereof.

* * * * *